(12) United States Patent
Lin et al.

(10) Patent No.: US 8,283,370 B2
(45) Date of Patent: Oct. 9, 2012

(54) IMIDAZOLIDINEDIONE DERIVATIVES AS ANTIMALARIAL AGENTS, PREPARATION THEREOF, AND METHODS OF USE

(75) Inventors: Ai Jeng Lin, North Potomac, MD (US); Michael P. Kozar, Monrovia, MD (US); Michael T. O'Neil, Jefferson, MD (US); Alan J. Magill, Kensington, MD (US); David L. Saunders, APO, AP (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/122,140

(22) PCT Filed: Oct. 2, 2009

(86) PCT No.: PCT/US2009/059455
§ 371 (c)(1), (2), (4) Date: Mar. 31, 2011

(87) PCT Pub. No.: WO2010/051129
PCT Pub. Date: May 6, 2010

(65) Prior Publication Data
US 2011/0230533 A1   Sep. 22, 2011

Related U.S. Application Data

(60) Provisional application No. 61/102,479, filed on Oct. 3, 2008.

(51) Int. Cl.
*A61K 31/4166* (2006.01)
*C07D 233/30* (2006.01)

(52) U.S. Cl. .................................. 514/390; 548/318.1

(58) Field of Classification Search ............... 548/318.1; 514/390
See application file for complete search history.

(56) References Cited

U.S. PATENT DOCUMENTS

| 4,791,229 A | 12/1988 | Fauss et al. |
| 2005/0148645 A1 | 7/2005 | Lin et al. |

OTHER PUBLICATIONS

Guan, Jian et al, "Malaria Causal Prophylactic Activity of Imidazolidinedione Derivatives," J. Med. Chem. (2007), 50(24), pp. 6226-6231.*
Corcoran et al., "Causal Prophylactic and Radical Curative Activity of WR182393 (A Guanylhydrazone) Against Plasmodium cynomolgi in *Macaca mufatta*," *Am. J. Trop Med. Hyg.*, 1993, 49(4): 473-477.
Guan et al., "Malaria Causal Prophylactic Activity of Imidazolidinedione Derivatives," *J. Med. Chem.*, 2007, 50(24): 6226-6231.
Guan et al., "Structure Identification and Prophylactic Antimalarial Efficacy of 2-guanidinoimidazolidinedione Derivatives," *Bioorg. Med. Chem.*, 2005, 13(3): 699-704.
Shanks et al., "A New Primaquine Analogue, Tafenoquine (WR 238605), for Prophylaxis Against Plasmodium falciparum Malaria," *Clin. Infect, Dis.*, 2001, 33: 1968-1974.
Zhang et al., "Unambiguous Synthesis and Prophylactic Antimalarial Activities of Imidazolidinedione Derivatives," *J. Med. Chem.*, 2005, 48(20): 6472-6481.
International Search Report and Written Opinion mailed Oct. 6, 2010 in PCT Application No. PCT/US2009/059455, filed Oct. 2, 2009.

* cited by examiner

*Primary Examiner* — Joseph K. McKane
*Assistant Examiner* — Janet L Coppins
(74) *Attorney, Agent, or Firm* — Marcus Streips

(57) ABSTRACT

Embodiments disclosed herein relate to new imidazolidinedione derivatives, methods of making these compounds, and methods of using the same to prevent, treat, or inhibit malaria in a subject.

20 Claims, No Drawings

IMIDAZOLIDINEDIONE DERIVATIVES AS ANTIMALARIAL AGENTS, PREPARATION THEREOF, AND METHODS OF USE

CROSS-REFERENCE TO RELATED APPLICATIONS

This application is the U.S. National Phase under 35 U.S.C. §371 of International Application No. PCT/US2009/059455, filed Oct. 2, 2009, designating the U.S. and published in English on May 6, 2010 as WO 2010/051129, which claims priority to U.S. Provisional Application No. 61/102,479, filed on Oct. 3, 2008. The content of these applications is incorporated herein by reference in their entireties.

FIELD OF THE INVENTION

Embodiments disclosed herein relate to new imidazolidinedione derivatives, methods of making these compounds, and methods of using the same to prevent, treat, or inhibit malaria in a subject.

BACKGROUND

There are approximately 350 to 500 million cases of malaria each year. The current global situation with respect to malaria infections is rapidly worsening mainly due to non-availability of effective drugs and development of drug resistance to the existing first line drugs, such as chloroquine and pyrimethamine (C. Plowe, *The Journal of Experimental Biology* 206, 3745-3752 (2003); A. Nzila, *J. Antimicrob. Chemother.* 57, 1043-H154 (2006)). In addition to the drug resistance of the first line antimalarial drugs, the usefulness of many newer antimalarial drugs was impaired by their side effects. Lethal hemolysis side effect was observed in glucose-6-phosphate dehydrogenase (G6PD) deficient recipients of 8-aminoquinoline drugs (primaquine and tafenoquine) (P. Carson et al., *Man. Bulletin of the World Health Organization* 59, 427-437 (1981); E. Beutler, *Blood,* 14 (2), 103-139 (1959)); and CNS toxicity was a problematic side effect in patients treated with mefloquine (P. Phillips-Howard et al., *Drug Safety* 12:370-383 (1995); P. Schlagenhauf, P *J Travel Med* 6:122-123 (1999); H. AlKadi, *Chemotherapy* 53:385-391 (2007)).

SUMMARY OF THE INVENTION

Various embodiments herein relate to a compound having formula I:

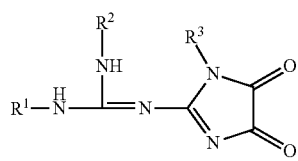

(I)

or a tautomer thereof, or their pharmaceutically acceptable salts,
wherein:
$R^1$ is aryl or heteroaryl, each optionally substituted with one or more $R^{1a}$;
each $R^{1a}$ is independently selected from the group consisting of hydroxyl, carboxyl, halo, aralkyl, amino, alkylamino, dialkylamino, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy, optionally substituted with up to 5 fluoro;
$R^2$ is an optionally substituted substituent selected from the group consisting of $C_{1-10}$ alkyl, $C_{2-10}$ alkenyl, $C_{3-10}$ cycloalkyl$(CH_2)_n$—, aryl$(CH_2)_n$—, heteroaryl$(CH_2)_n$—, alkylaryl, heterocyclyl$(CH_2)_n$—, aminoalkyl, $R^{2a}R^{2b}N(CH_2)_n$—, or $R^2$ is $R^4C(=O)$—, or $R^2$ is $R^5O$—;
n is an integer selected from 0, 1, 2, 3, 4, 5, 6, or 7;
$R^{2a}$ is selected from the group consisting of hydrogen, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy optionally substituted with up to 5 fluoro;
$R^{2b}$ is selected from the group consisting of hydrogen, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy optionally substituted with up to 5 fluoro;
$R^3$ is $C_{1-10}$ alkyl optionally substituted with up to 5 fluoro;
$R^4$ is selected from the group consisting of aryl, heteroaryl, $C_{3-7}$ cycloalkyl, and $C_{1-6}$ alkyl, each optionally substituted with up to 5 fluoro; and
$R^5$ is an optionally substituted substituent selected from the group consisting of $C_{1-10}$ alkyl, $C_{2-10}$ alkenyl, $C_{3-10}$ cycloalkyl$(CH_2)_n$—, aryl$(CH_2)_n$—, heteroaryl$(CH_2)_n$—, alkylaryl, heterocyclyl$(CH_2)_n$—, aminoalkyl, and $R^{2a}R^{2b}N(CH_2)_n$—.

In some embodiments,
$R^1$ is aryl optionally substituted with one or more $R^{1a}$;
each $R^{1a}$ is independently selected from the group consisting of halo, $C_{1-6}$ alkyl optionally substituted with up to 5 fluoro, and $C_{1-6}$ alkoxy, optionally substituted with up to 5 fluoro;
$R^2$ is an optionally substituted substituent selected from the group consisting of $C_{1-6}$ alkyl, $C_{2-6}$ alkenyl, $C_{3-7}$ cycloalkyl, aryl, heteroaryl, heterocyclyl$(CH_2)_n$—, aminoalkyl, $C_{1-10}$ alkylC$(=O)$—, $R^{2a}R^{2b}N(CH_2)_n$—, $C_{1-6}$ alkylO—, $C_{2-6}$ alkenylO—, $C_{3-10}$ cycloalkylO—, arylO—, heteroarylO—, heterocyclylO—, $C_{1-6}$ alkylC$(=O)O$—, and $R^{2a}R^{2b}N(CH_2)_nO$—,
n is an integer selected from 1, 2, 3, 4, 5, or 6;
$R^{2a}$ is selected from the group consisting of hydrogen, aryl, $C_{3-7}$ cycloalkyl, and $C_{1-6}$ alkyl optionally substituted with up to 5 fluoro, and $C_{1-6}$ alkoxy optionally substituted with up to 5 fluoro;
$R^{2b}$ is selected from the group consisting of alkoxycarbonyl, and $C_{1-6}$ alkyl optionally substituted with up to 5 fluoro; and
$R^3$ is $C_{1-6}$ alkyl.

In other embodiments,
$R^1$ is phenyl optionally substituted with one or more $R^{1a}$;
each $R^{1a}$ is independently selected from the group consisting of halo, $C_{1-3}$ alkyl optionally substituted with up to 5 fluoro, and $C_{1-3}$ alkoxy, optionally substituted with up to 5 fluoro;
$R^2$ is selected from the group consisting of $C_{1-6}$ alkyl, $C_{2-6}$ alkenyl, $C_{3-7}$ cycloalkyl, aryl, heteroaryl, heterocyclyl$(CH_2)_n$—, aminoalkyl, $C_{1-10}$ alkylC$(=O)$—, $R^{2a}R^{2b}N(CH_2)_n$—, $C_{1-6}$ alkylO—, $C_{2-6}$ alkenylO—, $C_{3-10}$ cycloalkylO—, arylO—, heteroarylO—, heterocyclylO—, $C_{1-6}$ alkylC$(=O)O$—, and $R^{2a}R^{2b}N(CH_2)_nO$—,
n is an integer selected from 1, 2, 3, 4, 5, or 6;

$R^{2a}$ is selected from the group consisting of hydrogen, and $C_{1-6}$ alkyl optionally substituted with up to 5 fluoro, and $C_{1-6}$ alkoxy optionally substituted with up to 5 fluoro;

$R^{2b}$ is selected from the group consisting of alkoxycarbonyl, and $C_{1-6}$ alkyl optionally substituted with up to 5 fluoro; and $R^3$ is $C_{1-4}$ alkyl.

In further embodiments, $R^1$ is aryl optionally substituted with one or more $R^{1a}$;

each $R^{1a}$ is independently selected from the group consisting of halo, $C_{1-6}$ alkyl optionally substituted with up to 5 fluoro, and $C_{1-6}$ alkoxy, optionally substituted with up to 5 fluoro;

$R^2$ is $R^4C(=O)-$, $R^4$ is selected from the group consisting of aryl, $C_{3-7}$ cycloalkyl, and $C_{1-6}$ alkyl, each optionally substituted with up to 5 fluoro; and $R^3$ is $C_{1-6}$ alkyl.

In some embodiments, $R^1$ is phenyl optionally substituted with one or more $R^{1a}$;

each $R^{1a}$ is independently selected from the group consisting of halo, $C_{1-3}$ alkyl optionally substituted with up to 5 fluoro, and $C_{1-3}$ alkoxy, optionally substituted with up to 5 fluoro;

$R^2$ is $R^4C(=O)-$, $R^4$ is selected from the group consisting of $C_{3-7}$ cycloalkyl, and $C_{1-6}$ alkyl, each optionally substituted with up to 3 fluoro; and $R^3$ is $C_{1-4}$ alkyl.

In other embodiments, $R^2$ is methyl, ethyl, isopropyl, tert-butyl, allyl, benzyl, neopentyl, or phenyl.

In some embodiments, $R^2$ is isopropyl.

In some embodiments, $R^2$ is $R^4C(=O)-$, and $R^4$ is methyl, ethyl, isopropyl, tert-butyl, allyl, benzyl, neopentyl, or phenyl.

In some embodiments, $R^4$ is tert-butyl.

In some embodiments, $R^1$ is aryl optionally substituted with one or more $R^{1a}$;

each $R^{1a}$ is independently selected from the group consisting of halo, $C_{1-6}$ alkyl optionally substituted with up to 5 fluoro, and $C_{1-6}$ alkoxy, optionally substituted with up to 5 fluoro;

$R^2$ is $R^5O-$, $R^5$ is selected from the group consisting of aryl, $C_{3-7}$ cycloalkyl, and $C_{1-6}$ alkyl, each optionally substituted with up to 5 fluoro; and $R^3$ is $C_{1-6}$ alkyl.

In other embodiments, $R^1$ is phenyl optionally substituted with one or more $R^{1a}$;

each $R^{1a}$ is independently selected from the group consisting of halo, $C_{1-3}$ alkyl optionally substituted with up to 5 fluoro, and $C_{1-3}$ alkoxy, optionally substituted with up to 5 fluoro;

$R^2$ is $R^5O-$, $R^5$ is selected from the group consisting of $C_{3-7}$ cycloalkyl, and $C_{1-6}$ alkyl, each optionally substituted with up to 3 fluoro; and $R^3$ is $C_{1-4}$ alkyl.

Various embodiments relate to a compound having the formula Ia:

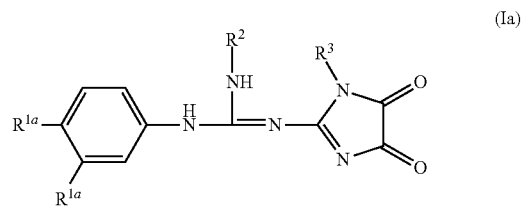

or a tautomer thereof, or their pharmaceutically acceptable salts.

Other embodiments relate to a compound having the formula Iaa:

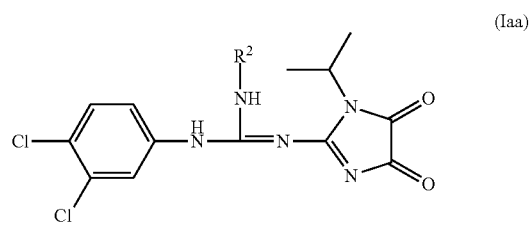

or a tautomer thereof, or their pharmaceutically acceptable salts, wherein:

$R^2$ is selected from the group consisting of $C_{1-6}$ alkyl, $C_{3-10}$ cycloalkyl, aryl, heteroaryl, heterocyclyl, $C_{3-10}$ cycloalkylCH$_2-$, arylCH$_2-$, heteroarylCH$_2-$, heterocyclylCH$_2-$, $R^{2a}R^{2b}N(CH_2)_n-$, n is an integer selected from 1, 2, 3, 4, 5, or 6;

$R^{2a}$ is selected from the group consisting of hydrogen, and $C_{1-6}$ alkyl optionally substituted with up to 5 fluoro, and $C_{1-6}$ alkoxy optionally substituted with up to 5 fluoro; and $R^{2b}$ is selected from the group consisting of alkoxycarbonyl, and $C_{1-6}$ alkyl optionally substituted with up to 5 fluoro.

In some embodiments, $R^2$ is methyl, ethyl, isopropyl, tert-butyl, allyl, benzyl, neopentyl, or phenyl.

In some embodiments, $R^2$ is isopropyl.

Further embodiments relate to a compound having the formula Ib:

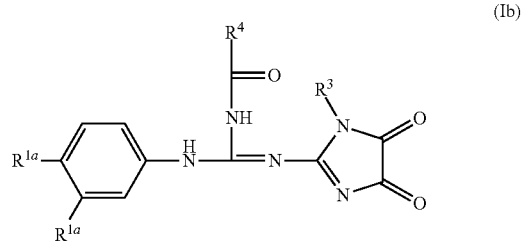

or a tautomer thereof, or their pharmaceutically acceptable salts.

Additional embodiments relate to a compound having the formula Ibb:

(Ibb)

or a tautomer thereof, or their pharmaceutically acceptable salts,
wherein:
R$^4$ is selected from the group consisting of C$_{1-6}$ alkyl, C$_{1-6}$ alkyl, C$_{3-10}$ cycloalkyl, aryl, heteroaryl, heterocyclyl, C$_{3-10}$ cycloalkylCH$_2$—, arylCH$_2$—, each optionally substituted with up to 3 fluoro.
In some embodiments, R$^4$ is methyl, ethyl, isopropyl, tert-butyl, benzyl, neopentyl, or phenyl.
In some embodiments, R$^4$ is tert-butyl.
Some embodiments relate to a compound having the formula Ic:

(Ic)

or a tautomer thereof, or their pharmaceutically acceptable salts.
Some embodiments relate to a compound having the formula Icc:

(Icc)

or a tautomer thereof, or their pharmaceutically acceptable salts,
wherein:
R$^5$ is selected from the group consisting of C$_{1-6}$ alkyl, C$_{1-6}$ alkyl, C$_{3-10}$ cycloalkyl, aryl, heteroaryl, heterocyclyl, C$_{3-10}$ cycloalkylCH$_2$—, arylCH$_2$—, each optionally substituted with up to 3 fluoro.
In some embodiments, R$^4$ is methyl, ethyl, isopropyl, tert-butyl, benzyl, neopentyl, or phenyl.
Further embodiments relate to a method for making a compound of formula II:

(II)

or a tautomer thereof, or their pharmaceutically acceptable salts,
comprising intermixing a compound of formula IIa:

(IIa)

with a compound of formula A:

(A)

in the presence of a base,
wherein:
the base is selected from the group consisting of triethyl amine, diisopropyul ethyl amine, dimethyl amino pyridine (DMAP), DBU, DBN, sodium carbonate, potassium carbonate, lithium carbonate, calcium carbonate, magnesium carbonate, sodium bicarbonate, potassium bicarbonate, lithium bicarbonate, and combinations thereof;
X is halo or R$^4$C(=O)O—;
R$^1$ is aryl or heteroaryl, each optionally substituted with one or more R$^{1a}$;
each R$^{1a}$ is independently selected from the group consisting of hydroxyl, carboxyl, halo, aralkyl, amino, alkylamino, dialkylamino, alkoxycarbonyl, alkylsulfonyl, heterocycle, aryl, C$_{3-7}$ cycloalkyl, C$_{1-6}$ alkyl optionally substituted with up to 5 fluoro, and C$_{1-6}$ alkoxy, optionally substituted with up to 5 fluoro;
R$^3$ is C$_{1-10}$ alkyl optionally substituted with up to 5 fluoro; and
R$^4$ is selected from the group consisting of aryl, heteroaryl, C$_{3-7}$ cycloalkyl, and C$_{1-6}$ alkyl, each optionally substituted with up to 5 fluoro.
In some embodiments,
the base is triethyl amine and DMAP;
X is —Cl (chloro);
R$^1$ is phenyl optionally substituted with one or more R$^{1a}$;
each R$^{1a}$ is independently selected from the group consisting of halo, C$_{1-3}$ alkyl optionally substituted with up to 5 fluoro, and C$_{1-3}$ alkoxy, optionally substituted with up to 5 fluoro;
R$^3$ is C$_{1-4}$ alkyl; and
R$^4$ is selected from the group consisting of aryl, C$_{3-7}$ cycloalkyl, and C$_{1-6}$ alkyl, each optionally substituted with up to 5 fluoro.

In some embodiments, $R^3$ is isopropyl.

Additional embodiments relate to method for making a compound of formula III:

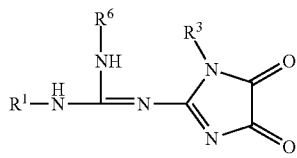

(III)

or a tautomer thereof, or their pharmaceutically acceptable salts, comprising intermixing a compound of formula IIIa:

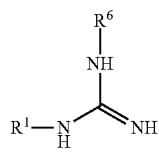

(IIIa)

with a compound of formula B:

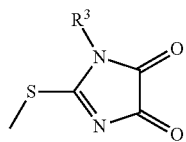

(B)

under heating conditions,
wherein:
$R^1$ is aryl or heteroaryl, each optionally substituted with one or more $R^{1a}$;
each $R^{1a}$ is independently selected from the group consisting of hydroxyl, carboxyl, halo, aralkyl, amino, alkylamino, dialkylamino, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy, optionally substituted with up to 5 fluoro;
$R^3$ is $C_{1-10}$ alkyl optionally substituted with up to 5 fluoro;
$R^6$ is selected from the group consisting of $C_{1-6}$ alkyl, $C_{3-10}$ cycloalkyl, aryl, heteroaryl, heterocyclyl, $C_{3-10}$ cycloalkylCH$_2$—, arylCH$_2$—, heteroarylCH$_2$—, heterocyclylCH$_2$—, $R^{6a}R^{6b}N(CH_2)_n$—;
n is an integer selected from 1, 2, 3, 4, 5, or 6;
$R^{6a}$ is selected from the group consisting of hydrogen, and $C_{1-6}$ alkyl optionally substituted with up to 5 fluoro, and $C_{1-6}$ alkoxy optionally substituted with up to 5 fluoro; and
$R^{6b}$ is selected from the group consisting of alkoxycarbonyl, and $C_{1-6}$ alkyl optionally substituted with up to 5 fluoro.

In some embodiments,
$R^1$ is aryl optionally substituted with one or more $R^{1a}$;
each $R^{1a}$ is independently selected from the group consisting of halo, $C_{1-6}$ alkyl optionally substituted with up to 5 fluoro, and $C_{1-6}$ alkoxy, optionally substituted with up to 5 fluoro;
$R^6$ is an optionally substituted substituent selected from the group consisting of $C_{1-6}$ alkyl, $C_{2-6}$ alkenyl, $C_{3-7}$ cycloalkyl, aryl, heteroaryl, heterocyclyl(CH$_2$)$_n$—, aminoalkyl, $C_{1-10}$ alkylC(=O)—, $R^{6a}R^{6b}N(CH_2)_n$—, $C_{1-6}$ alkylO—, $C_{2-6}$ alkenylO—, $C_{3-10}$ cycloalkylO—, arylO—, heteroarylO—, heterocyclylO—, $C_{1-6}$ alkylC(=O)O—, and $R^{6a}R^{6b}N(CH_2)_nO$—,
n is an integer selected from 1, 2, 3, 4, 5, or 6;
$R^{6a}$ is selected from the group consisting of hydrogen, aryl, $C_{3-7}$ cycloalkyl, and $C_{1-6}$ alkyl optionally substituted with up to 5 fluoro, and $C_{1-6}$ alkoxy optionally substituted with up to 5 fluoro;
$R^{6b}$ is selected from the group consisting of alkoxycarbonyl, and $C_{1-6}$ alkyl optionally substituted with up to 5 fluoro; and
$R^3$ is $C_{1-6}$ alkyl.

In some embodiments,
$R^1$ is phenyl optionally substituted with one or more $R^{1a}$;
each $R^{1a}$ is independently selected from the group consisting of halo, $C_{1-3}$ alkyl optionally substituted with up to 5 fluoro, and $C_{1-3}$ alkoxy, optionally substituted with up to 5 fluoro;
$R^6$ is selected from the group consisting of $C_{1-6}$ alkyl, $C_{2-6}$ alkenyl, $C_{3-7}$ cycloalkyl, aryl, heteroaryl, heterocyclyl (CH$_2$)$_n$—, aminoalkyl, $C_{1-10}$ alkylC(=O)—, $R^{6a}R^{6b}N$ (CH$_2$)$_n$—, $C_{1-6}$ alkylO—, $C_{2-6}$ alkenylO—, $C_{3-10}$ cycloalkylO—, arylO—, heteroarylO—, heterocyclylO—, $C_{1-6}$ alkylC(=O)O—, and $R^{6a}R^{6b}N$ (CH$_2$)$_n$O—,
n is an integer selected from 1, 2, 3, 4, 5, or 6;
$R^{2a}$ is selected from the group consisting of hydrogen, and $C_{1-6}$ alkyl optionally substituted with up to 5 fluoro, and $C_{1-6}$ alkoxy optionally substituted with up to 5 fluoro;
$R^{6b}$ is selected from the group consisting of alkoxycarbonyl, and $C_{1-6}$ alkyl optionally substituted with up to 5 fluoro; and
$R^3$ is $C_{1-4}$ alkyl.

In some embodiments, $R^3$ is isopropyl.

In other embodiments, the heating conditions include heating the mixture of a compound of formula IIIa and formula B in the range of from about 30° C. to about 250° C.

In some embodiments, the heating conditions include heating the mixture of a compound of formula IIIa and formula B in the range of from about 50° C. to about 150° C.

In more embodiments, the heating conditions include heating the mixture of a compound of formula IIIa and formula B in the range of from about 75° C. to about 125° C.

In some embodiments, the heating conditions include heating the mixture of a compound of formula IIIa and formula B at about 100° C.

Various embodiments relate to a method of treating, preventing, or inhibiting malaria or a disease or disorder associated with malaria or a *Plasmodium* parasite, comprising administering a therapeutically effective amount of at least one compound of any one of claims 1-22 to a subject in need thereof.

In some embodiments, the compound is administered intramuscularly, orally, or transdermally.

Some embodiments further include administering to the subject a supplementary active compound.

In some embodiments, the supplementary active compound is an antimalarial, an antibacterial, or an anti-inflammatory agent.

Other embodiments relate to a kit including at least one compound disclosed in embodiments herein and instructions for administering the compound.

Other embodiments relate to a composition including at least one compound disclosed in embodiments herein and a pharmaceutically acceptable carrier.

In some embodiments, the composition is suitable for oral administration, intramuscular administration, or transdermal administration.

Further embodiments relate to a compound as described herein, or a pharmaceutically acceptable equivalent or pharmaceutically acceptable salt thereof.

Additional embodiments relate to a compound represented by structural formula 5, 6 or 7,

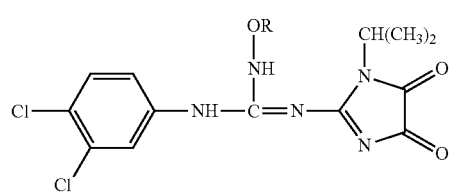

or a pharmaceutically acceptable equivalent or pharmaceutically acceptable salt of said compound;
wherein R is an optionally substituted substituent selected from the group consisting of alkyl, aryl, cycloalkyl, heterocycloalkyl, heteroaryl, alkylaryl, acyl, heterocyclic rings, and aminoalkyl.

In some embodiments, R is an optionally substituted substituent selected from the group consisting of alkyl, aryl, aminoalkyl, and hetrocyclic ring;
wherein the alkyl substituent or any alkyl portion of any of the substituents may be saturated or unsaturated and/or aliphatic or branched;
or a pharmaceutically acceptable equivalent or pharmaceutically acceptable salt of said compound.

In some embodiments, R is methyl, ethyl, isopropyl, t-butyl, allyl, benzyl, neopentyl, or phenyl.

In some embodiments, the compound is represented by structure 6, and R is isopropyl; or a pharmaceutically acceptable equivalent or pharmaceutically acceptable salt of the compound.

In some embodiments, the compound is represented by structure 7, and wherein R is t-butyl; or a pharmaceutically acceptable equivalent or pharmaceutically acceptable salt of the compound.

Further embodiments relate to a method of making a compound described in an embodiment herein, wherein the method is as illustrated and described herein.

In some embodiments, the compounds described herein include the proviso that $R^2$ is not $C_{1-6}$ alkyl, and $R^4$ is not $C_{1-6}$ alkyl.

In some embodiments, the compounds described herein include the proviso that R is not $C_{1-6}$ alkyl.

In some embodiments, the compounds described herein include the proviso that the compound is not selected from the group consisting of:

In some embodiments, the methods include the proviso that $R^4$ is not $C_{1-6}$ alkyl.

In some embodiments, the methods include the proviso that the compound of formula II is not selected from the group consisting of:

-continued

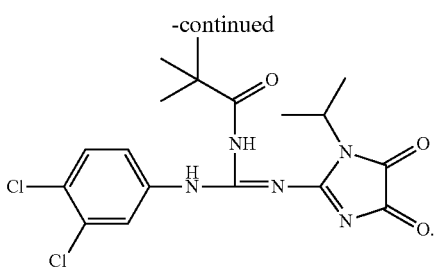

DETAILED DESCRIPTION OF THE PREFERRED EMBODIMENT

Embodiments disclosed herein relate to new imidazolidinedione derivatives with enhanced chemical and/or metabolic stability. Additional embodiments relate to the synthesis of these derivatives, and methods of using the same to prevent, treat, or inhibit malaria in a subject. The increased stability of the compounds described herein provide for increased antimalarial activity, for example by increased oral efficacy.

Compounds

Various embodiments relate to compounds encompassed by formulae I, II, III:

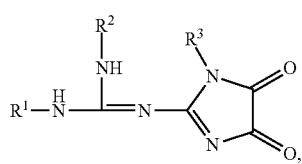
(I)

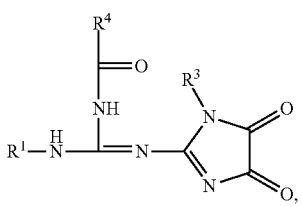
(II)

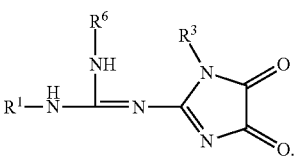
(III)

wherein:
$R^1$ is aryl or heteroaryl, each optionally substituted with one or more $R^{1a}$;
each $R^{1a}$ is independently selected from the group consisting of hydroxyl, carboxyl, halo, aralkyl, amino, alkylamino, dialkylamino, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy, optionally substituted with up to 5 fluoro;
$R^2$ is an optionally substituted substituent selected from the group consisting of $C_{1-10}$ alkyl, $C_{2-10}$ alkenyl, $C_{3-10}$ cycloalkyl$(CH_2)_n$—, aryl$(CH_2)_n$—, heteroaryl$(CH_2)_n$—, alkylaryl, heterocyclyl$(CH_2)_n$—, aminoalkyl, $R^{2a}R^{2b}N(CH_2)_n$—, or $R^2$ is $R^4C(=O)$—, or $R^2$ is $R^5O$—;
n is an integer selected from 0, 1, 2, 3, 4, 5, 6, or 7;
$R^{2a}$ is selected from the group consisting of hydrogen, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy optionally substituted with up to 5 fluoro;
$R^{2b}$ is selected from the group consisting of hydrogen, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy optionally substituted with up to 5 fluoro;
$R^3$ is $C_{1-10}$ alkyl optionally substituted with up to 5 fluoro;
$R^4$ is selected from the group consisting of aryl, heteroaryl, $C_{3-7}$ cycloalkyl, and $C_{1-6}$ alkyl, each optionally substituted with up to 5 fluoro;
$R^5$ is an optionally substituted substituent selected from the group consisting of $C_{1-10}$ alkyl, $C_{2-10}$ alkenyl, $C_{3-10}$ cycloalkyl$(CH_2)_n$—, aryl$(CH_2)_n$—, heteroaryl$(CH_2)_n$—, alkylaryl, heterocyclyl$(CH_2)_n$—, aminoalkyl, and $R^{2a}R^{2b}N(CH_2)_n$—.
$R^6$ is selected from the group consisting of $C_{1-6}$ alkyl, $C_{3-10}$ cycloalkyl, aryl, heteroaryl, heterocyclyl, $C_{3-10}$ cycloalkylCH$_2$—, arylCH$_2$—, heteroarylCH$_2$—, heterocyclylCH$_2$—, $R^{6a}R^{6b}N(CH_2)_n$—;
n is an integer selected from 1, 2, 3, 4, 5, or 6;
$R^{6a}$ is selected from the group consisting of hydrogen, and $C_{1-6}$ alkyl optionally substituted with up to 5 fluoro, and $C_{1-6}$ alkoxy optionally substituted with up to 5 fluoro; and
$R^{6b}$ is selected from the group consisting of alkoxycarbonyl, and $C_{1-6}$ alkyl optionally substituted with up to 5 fluoro.

Some embodiment relate to a subset of compounds encompassed by Formula I. For example, various embodiments relate to chemically stable derivatives of compound 1 as represented herein by structures 5, 6 and 7:

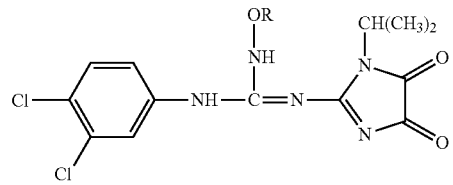
5

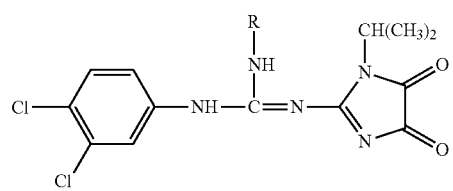
6

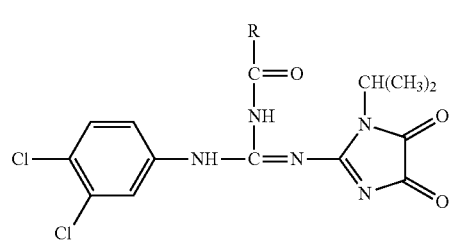
7 wherein R is an alkyl, aryl, cycloalkyl, heterocycloalkyl, heteroaryl, alkylaryl, acyl, heterocyclic rings, aminoalkyl, and wherein R can be substituted or unsubstituted. It is intended that compounds within the scope of embodiments described herein include pharmaceutically acceptable salts of these as well.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which can be unsubstituted (i.e., contain only carbon and hydrogen) or substituted by one or more suitable substituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3-14 carbon ring atoms, each of which can be saturated or unsaturated, and which can be unsubstituted or substituted by one or more suitable substituents as defined below, and to which can be fused one or more heterocycloalkyl groups, aryl groups, or heteroaryl groups, which themselves can be unsubstituted or substituted by one or more substituents.

A "heterocycloalkyl" is intended to mean a non-aromatic monovalent monocyclic, bicyclic, or tricyclic radical, which is saturated or unsaturated, comprising 3 18 ring members, which includes 1 5 heteroatoms selected from nitrogen, oxygen, and sulfur, where the radical is unsubstituted or substituted by one or more suitable substituents as defined below, and to which can be fused one or more cycloalkyl groups, aryl groups, or heteroaryl groups, which themselves can be unsubstituted or substituted by one or more suitable substituents.

An "aryl" is intended to mean an aromatic monovalent monocyclic, bicyclic, or tricyclic radical comprising 6, 10, 14, or 18 carbon ring members, which can be unsubstituted or substituted by one or more suitable substituents as defined below, and to which can be fused one or more cycloalkyl groups, heterocycloalkyl groups, or heteroaryl groups, which themselves can be unsubstituted or substituted by one or more suitable substituents. Thus, the term "aryl group" includes a benzyl group (Bzl).

A "heteroaryl" is intended to mean an aromatic monovalent monocyclic, bicyclic, or tricyclic radical comprising 4 18 ring members, including 1 5 heteroatoms selected from nitrogen, oxygen, and sulfur, which can be unsubstituted or substituted by one or more suitable substituents as defined below, and to which can be fused one or more cycloalkyl groups, heterocycloalkyl groups, or aryl groups, which themselves can be unsubstituted or substituted by one or more suitable substituents.

An "aralkyl" as used herein mean one or more aryl groups appended to an alkyl radical. Examples of aralkyl groups include, but are not limited to, benzyl, phenethyl, phenpropyl, phenbutyl, and the like.

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2, 4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)— Ra radical, where Ra is a suitable substituent as defined below.

A "thioacyl" is intended to mean a —C(S)— Ra radical, where Ra is a suitable substituent as defined below.

A "sulfonyl" is intended to mean a —SO$_2$Ra radical, where Ra is a suitable substituent as defined below.

A "hydroxyl" is intended to mean the radical —OH.

An "amino" is intended to mean the radical —NH$_2$.

An "alkylamino" is intended to mean the radical —NHR$^a$, where R$^a$ is an alkyl group.

A "dialkylamino" is intended to mean the radical —NR$^a$R$^b$, where R$^a$ and R$^b$ are each independently an alkyl group.

An "alkoxyl" is intended to mean the radical —OR$^a$, where R$^a$ is an alkyl group. Exemplary alkoxyl groups include methoxyl, ethoxyl, propoxyl, and the like.

An "alkoxycarbonyl" is intended to mean the radical —C(O)OR$^a$, where R$^a$ is an alkyl group.

An "alkylsulfonyl" is intended to mean the radical —SO2R$^a$, where R$^a$ is an alkyl group.

An "alkylaminocarbonyl" is intended to mean the radical —C(O)NHR$^a$, where R$^a$ is an alkyl group.

A "dialkylaminocarbonyl" is intended to mean the radical —C(O)NR$^a$R$^b$, where R$^a$ and R$^b$ are each independently an alkyl group.

A "mercapto" is intended to mean the radical —SH.

An "alkylthio" is intended to mean the radical —SR$^a$, where R$^a$ is an alkyl group.

A "carboxyl" is intended to mean the radical —C(O)OH.

A "carbamoyl" is intended to mean the radical —C(O)NH$_2$.

An "aryloxyl" is intended to mean the radical —ORc, where R$^c$ is an aryl group.

A "heteroaryloxyl" is intended to mean the radical —OR$^d$, where R$^d$ is a heteroaryl group.

An "arylthio" is intended to mean the radical —SR$^c$, where R$^c$ is an aryl group.

A "heteroarylthio" is intended to mean the radical —SR$^d$, where R$^d$ is a heteroaryl group.

A "heteroarylthio" is intended to mean the radical —SR$^d$, where R$^d$ is a heteroaryl group.

A "halo" is intended to mean fluoro, chloro, bromo, or iodo. A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups can be routinely selected by those skilled in the art in light of the functionality and particular chemistry used to construct the compound. Examples of suitable protecting groups are described, for example, in Greene and Wuts, Protective Groups in Organic Synthesis, 3rd edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae can be "optionally substituted" by one or more suitable "substituents". The term "substituent" or "suitable substituent" is intended to mean any suitable substituent that can be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which can be monocyclic or fused or non-fused polycyclic (e.g., cyclopropyl, cyclobutyl, cyclopentyl, or cyclohexyl), or a heterocycloalkyl, which can be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties can also be optionally substituted by a fused-ring structure or bridge, for example $OCH_2$—O. All of these substituents can optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups can be unsubstituted or substituted (i.e., they are optionally substituted) unless indicated otherwise herein (e.g., by indicating that the specified group is unsubstituted).

It is understood that while a compound of the general structural formulas herein can exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the disclosed embodiments can exist as single stereoisomers (i.e., essentially free of other stereoisomers), racemates, or mixtures of enantiomers, diastereomers, or both. All such single stereoisomers, racemates and mixtures thereof are intended to be within the scope of the embodiments described herein. Preferably, compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds in combination with water, isopropanol, ethanol, methanol, dimethyl sulfoxide, ethyl acetate, acetic acid, ethanolamine, or acetone. Also included are miscible formulations of solvate mixtures such as a compound in combination with an acetone and ethanol mixture. In a preferred embodiment, the solvate includes a compound in combination with about 20% ethanol and about 80% acetone. Thus, the structural formulas include compounds having the indicated structure, including the hydrated as well as the non-hydrated forms.

As indicated above, the compounds described herein also include active tautomeric and stereoisomeric forms of the compounds, which can be readily obtained using techniques known in the art. For example, optically active (R) and (S) isomers can be prepared via a stereospecific synthesis, e.g., using chiral synthons and chiral reagents, or racemic mixtures can be resolved using conventional techniques.

Preferred compounds within the scope of the embodiments described herein are those wherein R is an alkyl.

Specific examples of compounds within the scope of the present embodiments are set forth in Table 3 (Compounds 5a-5e), Table 4 (Compounds 6a-6n and 6p), and Scheme 2 (Compounds 7a, 7b and 7c).

In addition, it is understood that while a compound of the general structural formulas herein can exhibit the phenomenon of tautomerism, the structural formulas within this specification are expressly depicted in only one of the possible tautomeric forms. It is, therefore, to be understood that the structural formulas herein are intended to represent any tautomeric form of the depicted compound and is not to be limited merely to a specific compound form depicted by the structural formulas.

Synthesis of Compounds

Scheme 1 provides for the general preparation of derivative compounds represented by structures 5 and 6. In general, compounds represented by structures 5 and 6 were prepared by heating of the corresponding 3,4-dichlorophenylguanidines (compound 10 or 11—corresponding based on R substituent—i.e., N-alkoxyl or N-alkyl-3,4-dichlorophenylguanidine and isopropyl-2-methylsulfanyl-1H-imidazole-4,5-dione (compound 8) in chloroform in a sealed tube at 100° C. for 48-72 hr as shown in Scheme 1:

Scheme 1: Synthesis of Compounds 5 and 6

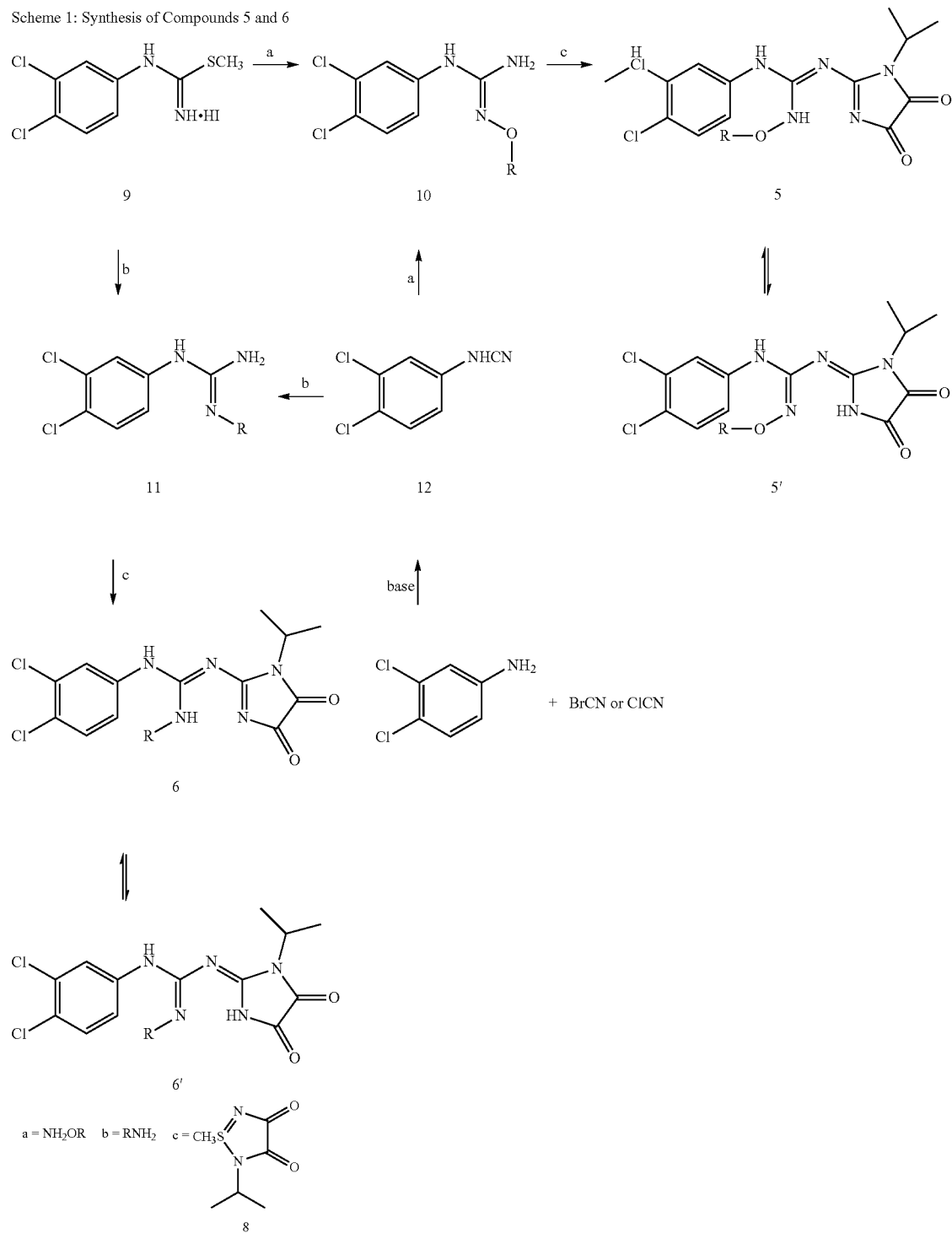

a = NH₂OR   b = RNH₂   c = CH₃S-[compound 8]

Compounds 5' and 6' are tautomers of 5 and 6, respectively. Tautomers differ in ways the double bonds are placed in the molecule and are considered the same compound.

The corresponding 3,4-dichlorophenylguanidines 10 and 11 were prepared by two methods, in turn, by either treating 1-(3,4-dichlorophenyl)-2-methylisothiourea hydroiodide (compound 9) (Method 1), or (3,4-dichlorophenyl)cyanamide (compound 12) (Method 2) with the corresponding amines (i.e., alkyl- or alkoxylamine). Method 2 is superior to Method 1 in yield and work-up. No column chromatography was needed in the purification of compounds 10 and 11 when Method 2 was used.

A more detailed description of the general procedure for synthesizing compounds 10 and 11 is set forth below.

Synthesis of starting materials isopropyl-2-methylsulfanyl-1H-imidazole-4,5-dione (compound 8) and compound 9 have been described previously (Q. Zhang et al., *J. Med. Chem.* 48 (20): 6472-6481 (2005), herein incorporated by reference in its entirety). Compound 12 was prepared according to a reported procedure set forth in U.S. Pat. No. 4,791,229, herein incorporated by reference in its entirety.

Substituent "R" is described above, and is intended to have the same meaning throughout the description of the embodiments disclosed herein.

Scheme 2 illustrates the general preparation of derivative compounds represented by Structure 7.

Scheme 2: Synthesis of Carboxamide Derivatives 7a-c:

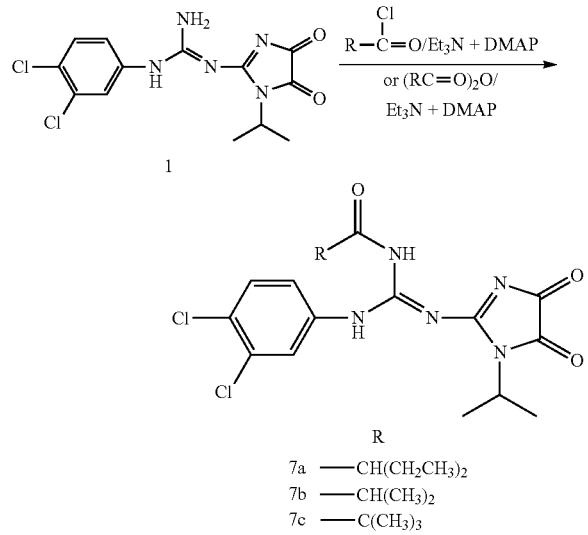

7a —CH(CH$_2$CH$_3$)$_2$
7b —CH(CH$_3$)$_2$
7c —C(CH$_3$)$_3$

Synthesis of compounds 7a-c are accomplished by treatment of compound 1 with acyl chloride or acid anhydrides in chloroform under the catalysis of 4-dimethylaminopyridine (DMAP) and triethylamine (Et$_3$N) as shown in Scheme 2. The method works well for the preparation of compounds 7a and 7b using acyl chloride as acylating agent. However, some acyl chlorides are too reactive to handle and not commercially available. In that case, acid anhydride (trimethylacetic anhydride) was used to make the desired carboxamide 7c.

Synthesis of starting material compound 1 has been previously described (Q. Zhang et al., *J. Med. Chem.* 48 (20): 6472-6481 (2005)).

Compounds 10a-e were synthesized according to the following general procedure. A mixture of 3,4-dichlorophenylcyanamide (1.0 eq.) (compound 12), which was prepared according to the procedure described in U.S. Pat. No. 4,791,229, triethylamine (4.0 eq.) and the corresponding alkoxylamine HCl salt (2.0 eq.) (or, more generally, —NHOR, where R is a substituent defined in Scheme 1 herein) in absolute alcohol was heated under reflux for 18 h. The solvent was removed under reduced pressure. Saturated aqueous Na$_2$CO$_3$ was added to the residue. The mixture was extracted with ethyl acetate. The organic extracts were combined, washed with brine, dried over Na$_2$SO$_4$, filtered, and the solvent was removed under reduced pressure. The residue was then suspended in small amount of cold (~4° C.) CH$_2$Cl$_2$, filtered and washed with CH$_2$Cl$_2$ to give a white solid.

Melting points were determined on a Mettler FP62 melting point apparatus and are uncorrected. Analytical thin-layer chromatography (TLC) was performed using HPTLC-HLF normal phase 150 micron silica gel plates (Analtech, Newark, Del.). Visualization of the developed chromatogram was performed by UV absorbance or by staining with iodine vapor. Liquid chromatography was performed using a Horizon HPFC System (Biotage, Charlottesville, Va.) with Flash 25M or 40M cartridges (KP-Sil Silica, 32-63 µm, 60 A°). Preparative TLC was performed using silica gel GF tapered uniplates (Analtech, Newark, Del.). $^1$H NMR and $^{13}$C NMR spectra were recorded in deuteriochloroform, unless otherwise noted, on a Bruker Avance 300 spectrometer (Bruker Instruments, Inc, Wilmington, Del.). Chemical shifts are reported in parts per million on the δ scale from an internal standard of tetramethylsilane. When the compounds formed two tautomers, the chemical shifts with * indicated the peaks were shared by both tautomers in NMR spectra. Combustion analyses were performed by Atlantic Microlab, Inc. (Norcross, Ga.). Where analyses are indicated by symbols of the elements, the analytical results obtained were within ±0.4% of the theoretical values. Mass analysis based on electron impact (EI) was done on a Hewlett Packard (Agilent; Santa Clara, Calif.) 5973 Mass Selector adapted with a HPP7 Direct Insertion Probe (Scientific Instrument Services; Ringoes, N.J.) using a steep temperature gradient at either low voltage (5 eV) to identify masses present or high voltage (70 eV) to obtain fragmentation data. An LC/UV-VIS/Trap MS was also employed for purity analysis and chromophore properties. The system consisted of an Agilent 1100 Series LC-UV/VIS system online with a ThermoF'innigan (now ThermoFisher; Waltham, Mass.) LeQ MS equipped with electrospray ionization (ESI) source. Samples were analyzed using shallow acetonitrile: 1% HCOOH/H$_2$O gradients at low flow rate.

The physical properties of the compounds 10a-e are listed in Table 1.

TABLE 1

Physical Properties of Compounds 10a-e

| Compound | R | Yield | Mp(° C.) | MS (m/z) |
|---|---|---|---|---|
| 10a | —CH$_3$ | 46 | 134 | 234 |
| 10b | —CH$_2$CH$_3$ | 54 | 124 | 247 |
| 10c | —CH$_2$CH═CH$_2$ | 72 | 90 | 259 |
| 10d | —C(CH$_3$)$_3$ | 41 | 126 | 275 |
| 10e | —CH$_2$C$_6$H$_5$ | 55 | 105 | — |

10a: $^1$H NMR (CD$_3$OD): δ 3.69 (s, 3H), 7.11 (dd, J=8.8 Hz and 2.6 Hz, 1H), 7.28 (d, J=8.8 Hz, 1H), 7.56 (d, J=2.6 Hz, 1H).

10b: $^1$H NMR (CDCl$_3$): δ 1.28 (t, J=6.98 Hz, 3H), 3.96 (q, J=6.85 Hz, 2H), 4.00 (br s, 2H), 6.97 (br d, J=7.44 Hz, 1H), 7.30 (s, 1H), 7.34 (d, J=2.31 Hz, 1H).

10c: $^1$H NMR (CDCl$_3$): δ 4.39-4.45 (m, 2H), 4.55 (br s, 2H), 5.78 (br s, 1H), 5.24 (dd, J=10.4 Hz and 1.4 Hz, 1H), 5.33 (dd, J=10.4 Hz and 1.4 Hz, 1H), 5.98-6.09 (m, 1H), 6.95 (dd, J=8.7 Hz and 2.6 Hz, 1H), 7.27 (d, J=8.7 Hz, 1H), 7.33 (d, J=2.6 Hz, 1H).

10d: $^1$H NMR (CDCl$_3$): δ 1.30 (s, 3H), 6.96 (dd, J=8.8 Hz and 2.6 Hz, 1H), 7.27 (d, J=8.8 Hz, 1H), 7.41 (d, J=2.6 Hz, 1H).

10e: ¹H NMR (CDCl₃): δ 4.93 (s, 2H), 6.89 (dd, J=8.6 Hz and 2.3 Hz, 1H), 7.23-7.42 (m, 7H).

Compound 11 was synthesized according to the following general procedures. Method 1: A mixture of 1-(3,4-dichlorophenyl)-2-methylisothiourea HI salt (1.0 eq.) (compound 9 which was prepared according to the procedure previously reported (Q. Zhang et al., *J. Med. Chem.* 48 (20): 6472-6481 (2005)) and 5-10 equivalent molar of the corresponding, for example, alkylamine (or, more generally, RNH₂, where R is a substituent defined in Scheme 1) in methanol was heated in a sealed tube at 80-100° C. for 18 h. The solvent and excess amine was removed under reduced pressure. Saturated aqueous Na₂CO₃ was added to the residue. The mixture was extracted with ethyl acetate. The organic extracts were combined, washed with brine, dried over Na₂SO₄, filtered, and the solvent was removed under reduced pressure. The residue was suspended in cold (~4° C.) CH₂Cl₂, filtered and washed with CH₂Cl₂ to give a white solid of compound 11 a-n and 11p in yield of 10-15%. The physical properties of the compounds 11a-n and 11p are listed in Table 2.

Method 2: A mixture of 3,4-dichlorophenylcyanamide (1.0 eq.) (compound 12) and the corresponding, for example, alkylamines (or, more generally, RNH₂, where R is a substituent defined in Scheme 1) (2.0 eq.) in absolute alcohol was heated in a sealed tube at 100° C. for 18 h. The solvent and excess amine was removed under reduced pressure. The residue was purified via recrystallization in Hexane/CH₂Cl₂ to give a light brown solid in 80-85% yield.

No column purification was needed in Method 2 which provided a higher yield than Method 1. The compound 11 prepared by both methods are identical in NMR and LC/MS.

TABLE 2

Physical Properties of Compound 11

| Compound | R | Yield (%) | Mp(° C.) | MS (m/z) |
|---|---|---|---|---|
| 11a | —CH₃ | 77 | 156 | 217 |
| 11b | —CH₂CH₃ | 76 | 129 | 231 |
| 11c | —CH₂CH₃ | 92 | 179 | 245 |
| 11d | —C(CH₃)₃ | 74 | 149 | 259 |
| 11e | —CH₂C(CH₃)₃ | 78 | 107 | 274 |
| 11f | —C₆H₅ | 73 | 192 | 279 |
| 11g | —CH₂C₆H₅ | 88 | 126 | 293 |
| 11h | —(CH₂)₅CH₃ | 95 | N/A - oil | 287 |
| 11i | 2-Adamantyl | 55 | 212 | 337 |
| 11j | —(CH₂)₂—N(CH₃)₂ | 61 | brown liquid | 275 |
| 11k | —(CH₂)₂N(CH₂CH₃)₂ | 77 | yellow liquid | 303 |
| 11l | —(CH₂)₃—N(pyrrolidinyl) | 46 | 146 | 301 |
| 11m | —(CH₂)₄—NMe₂ | 52 | 90 | 288 |
| 11n | —(CH₂)₄—N(pyrrolidinyl) | 68 | brown liquid | 329 |
| 11p | —(CH₂)₆NH_t-Boc* | 67 | N/A - oil | 402 |

*t-Boc = tert-Butoxycarbonyl-)

The NMR data of compounds 11a-n and 11p are listed as follows:

11a: ¹H NMR (CDCl₃): δ 2.87 (s, 3H), 3.72 (br s, 3H), 6.78 (d, J=8.5 Hz, 1H), 7.05 (s, 1H), 7.32 (d, J=8.5 Hz, 1H).

11b: ¹H NMR (CDCl₃): δ 1.22 (t, J=7.2 Hz, 3H), 3.27 (q, J=7.2 Hz, 2H), 6.79 (dd, J=8.4 Hz and 2.4 Hz, 1H), 7.05 (d, J=2.4 Hz, 1H), 7.33 (d, J=8.4 Hz, 1H).

11c: ¹H NMR (CD₃OD): δ 1.30 (d, J=6.4 Hz, 6H), 3.86 (q, J=6.4 Hz, 1H), 7.22 (dd, J=8.6 Hz and 2.4 Hz, 1H), 7.48 (d, J=2.4 Hz, 1H), 7.60 (d, J=8.6 Hz, 1H).

11d: ¹H NMR (CD₃OD): δ 1.34 (s, 9H), 6.70 (dd, J=8.4 Hz and 2.4 Hz, 1H), 6.91 (d, J=2.4 Hz, 1H), 7.14 (d, J=8.4 Hz, 1H).

11e: ¹H NMR (CDCl₃): δ 0.95 (s, 9H), 3.00 (s, 2H), 4.11 (br s, 3H), 6.77 (dd, J=8.5 Hz and 2.7 Hz, 1H), 7.03 (d, J=2.7 Hz, 1H), 7.31 (d, J=8.5 Hz, 1H).

11f: ¹H NMR (CD₃OD): δ 6.98-7.03 (m, 2H), 7.21-7.37 (m, 6H).

11g: ¹H NMR (CDCl₃): δ 4.40 (s, 2H), 6.76 (dd, J=8.5 Hz and 2.4 Hz, 1H), 7.03 (d, J=2.5 Hz, 1H), 7.26-7.37 (m, 6H).

11h: ¹H NMR (CDCl₃): δ 0.89 (t, J=6.5 Hz, 3H), 1.30 (br s, 6H), 1.52 (br s, 2H), 3.11-3.20 (m, 2H), 6.77 (dd, J=8.5 Hz and 2.7 Hz, 1H), 7.02 (d, J=2.7 Hz, 1H), 7.30 (d, J=8.5 Hz, 1H).

11i: ¹H NMR (CDCl₃): δ 1.62-2.05 (m, 15H), 3.73 (s, 1H), 6.79 (dd, J=8.5 Hz and 2.4 Hz, 1H), 7.02 (d, J=2.4 Hz, 1H), 7.32 (d, J=8.5 Hz, 1H).

11j: ¹H NMR (CDCl₃): δ 2.25 (s, 6H), 2.46 (t, J=5.2 Hz, 2H), 3.25 (t, J=5.2 Hz, 2H), 4.73 (br s, 3H), 6.76 (dd, J=8.5 Hz and 2.4 Hz, 1H), 7.03 (d, J=2.4 Hz, 1H), 7.29 (d, J=8.5 Hz, 1H).

11k: ¹H NMR (CDCl₃): δ 1.00 (t, J=7.2 Hz, 6H), 2.50 (m, 6H), 3.20 (t, J=4.0 Hz, 2H), 5.17 (br s, 2H), 6.75 (dd, J=8.5 Hz and 2.4 Hz, 1H), 7.01 (d, J=2.4 Hz, 1H), 7.29 (s, 1H).

11l: ¹H NMR (CDCl₃): δ 1.77 (br s, 4H), 2.56 (br s, 4H), 2.66 (t, J=5.2 Hz, 2H), 3.28 (t, J=5.2 Hz, 2H), 6.77 (dd, J=8.4 Hz and 2.2 Hz, 1H), 7.03 (d, J=2.2 Hz, 1H), 7.34 (d, J=8.4 Hz, 1H).

11m: ¹H NMR (CDCl₃): δ 1.65 (br s, 2H), 2.16 (s, 6H), 2.37 (t, J=5.5 Hz, 2H), 3.26 (t, J=5.5 Hz, 2H), 6.77 (br d, J=8.1 Hz, 1H), 7.03 (br s, 1H), 7.29 (br d, J=8.1 Hz, 1H).

11n: ¹H NMR (CDCl₃): δ 1.60 (m, 4H), 1.76 (br s, 4H), 2.48 (br s, 6H), 3.19 (t, J=6.5 Hz, 2H), 4.05 (br s, 2H), 6.75 (dd, J=8.4 Hz and 2.4 Hz, 1H), 7.02 (d, J=2.4 Hz, 1H), 7.27 (d, J=8.4 Hz, 1H).

11p: ¹H NMR (CDCl₃): δ 1.30-1.60 (m, 8H), 1.44 (s, 9H), 3.09-3.1.6 (m, 2H), 3.21 (t, J=6.9 Hz, 2H), 6.77 (dd, J=8.5 Hz and 2.4 Hz, 1H), 7.03 (d, J=2.4 Hz, 1H), 7.30 (d, J=8.4 Hz, 1H)

Compounds 5a-e were synthesized according to the following general procedure. A mixture of the corresponding guanidine 10 (see Table 1, above) (1.0 eq.) and 1.1-1.5 eq. of dione 8 in anhydrous CHCl₃ was heated in a sealed tube at 100° C. for 48-60 hours. The solvent was removed under reduced pressure. The residue was purified via a silica gel column chromatography. Chloroform (CHCl₃) was used as eluent for the purification of compounds 5a-e with yield ranging from 10-70%. Compounds were further purified by recrystallization from CH₂Cl₂/hexane. Physical properties of the final products are listed in Table 3. NMR, LC/MS and elemental analysis results are listed below:

TABLE 3

Imidazolidinedione Derivatives Represented by Structures 5

| No. | WR# | R | Yield (%) | MP(° C.) | MS (m/z) | Elemental Analysis |
|-----|--------|-----------------------|-----|-----|-------------|---------------|
| 5a  | 308143 | —CH$_3$               | 20  | 156 | 371 (M$^+$) | C•H•N•Cl |
| 5b  | 308145 | —CH$_3$CH$_2$         | 48  | 155 | 385 (M$^+$) | C•H•N•Cl |
| 5c  | 308163 | —CH$_3$CH═CH$_2$      | 10  | 266 | 397 (M$^+$) | C•H•N•Cl |
| 5d  | 308144 | —C(CH$_3$)$_3$        | 70  | 250 | 413 (M$^+$) | C•H•N•Cl |
| 5e  | 301795 | —CH$_2$C$_6$H$_5$     | 20  | 174 | 447 (M$^+$) | C•H•N•Cl |

N-Methoxy Derivatives of Compound 1 (5a): $^1$H NMR (CDCl$_3$) δ 1.45 (d, J=7.0 Hz, 6H), 3.88 (s, 3H), 4.55 (q, J=7.0 Hz, 1H), 6.94 (dd, J=8.6 Hz and 2.5 Hz, 1H), 7.12 (br s, 1H), 7.35 (d, J=8.6 Hz, 1H), 7.46 (s, 2.5 Hz, 1H); $^{13}$C NMR (CDCl$_3$): δ 19.5, 45.8, 62.3, 121.1, 124.1, 127.1, 130.2, 132.4, 137.6, 145.5, 149.6, 155.8, 155.9. Anal. calcd for (C$_{14}$H$_{15}$Cl$_2$N$_5$O$_3$): C, 45.18; H, 4.06; N, 18.82; Cl, 19.05. Found: C, 45.46; H, 4.10; N, 18.80; Cl, 19.21. MS (m/z): 385.00 (M$^+$), N-Ethoxy Derivatives of Compound 1 (5b): $^1$H NMR (CDCl$_3$): δ 10.52 (br s, 1H), 7.46 (d, J=2.51 Hz, 1H), 7.34 (d, J=8.65 Hz, 1H), 7.13 (br s, 1H), 6.95 (dd, J=8.67 and 2.59 Hz, 1H), 4.54 (m, 1H), 4.1 0 (q, J=6.99 Hz, 1H), 1.45 (d, J=6.96 Hz, 6H), 1.31 (t, J=7.02 Hz, 3H); $^{13}$C NMR (CDCl$_3$); 155.95, 155.80, 149.48, 145.45, 137.71, 132.38, 130.19, 126.98, 124.08, 121.15, 70.10, 45.78, 19.53, 14.63; Anal. calcd for (C$_{15}$H$_{17}$Cl$_2$N$_5$O$_3$): C, 46.65; H, 4.44; Cl, 18.36; N, 18.13. Found: C, 46.49; H, 4.35; Cl, 18.54; N, 17.83. MS (m/z): 385 (M$^+$)

N-Allyloxy Derivatives of Compound 1 (5c): $^1$H NMR (CDCl$_3$) δ 1.45 (d, J=7.0 Hz, 6H), 4.52-4.57 (m, 3H), 5.32-5.41 (m, 2H), 5.96-6.09 (m, 1H), 6.95 (dd, J=8.6 Hz and 2.5 Hz, 1H), 7.14 (br s, 1H), 7.33 (d, J=8.6 Hz, 1H), 7.47 (d, J=2.5 Hz, 1H), $^{13}$C NMR (CDCl$_3$): δ 19.5, 45.8, 75.3, 77.2, 118.8, 121.2, 124.1, 127.1, 130.2, 132.4, 134.0, 137.6, 145.7, 149.7, 155.7, 155.9. Anal. calcd for (C$_{16}$H$_{17}$Cl$_2$N$_5$O$_3$): C, 48.25; H, 4.30; N, 17.59; Cl, 17.80. Found: C, 48.41; H, 4.36; N, 17.55; Cl, 18.03. MS (m/z): 397 (M$^+$).

N-t-Butyloxy Derivatives of Compound 1 (5d): $^1$H NMR (CDCl$_3$) δ 1.36 (s, 9H), 1.46 (d, J=7.0 Hz, 6H), 4.56 (q, J=7.0 Hz, 1H), 6.97 (dd, J=8.6 Hz and 2.5 Hz, 1H), 7.15 (br s, 1H), 7.34 (d, J=8.6 Hz, 1H), 7.47 (d, J=2.5 Hz, 1H), $^{13}$C NMR (CDCl$_3$): δ 19.52, 27.69, 45.74, 79.36, 121.09, 123.98, 126.73, 130.12, 132.30, 137.87, 145.33, 149.11, 155.84, 156.04. Anal. calcd for (C$_{17}$H$_{21}$Cl$_2$N$_5$O$_3$): C, 49.29; H, 5.11; N, 16.90; Cl, 17.12. Found: C, 49.14; H, 5.14; N, 16.67; Cl, 17.32. MS (m/z): 413 (M$^+$).

N-Benzyloxy Derivatives of Compound 1 (5e): $^1$H NMR (CDCl$_3$) δ 1.43 (d, J=7.0 Hz, 6H), 4.50 (q, J=7.0 Hz, 1H), 5.05 (s, 2H), 6.93 (dd, J=8.6 Hz, and 2.7 Hz, 1H), 7.14 (br s, 1H), 7.33 (d, J=8.6 Hz, 1H), 7.39-7.44 (m, 5H). $^{13}$C NMR (CDCl$_3$): δ 19.7, 46.0, 76.8, 121.4, 124.3, 124.4, 127.4, 128.8, 129.0, 130.4, 132.6, 137.2, 137.7, 146.0, 150.0, 155.8, 156.2. Anal. calcd for (C$_{20}$H$_{19}$Cl$_2$N$_5$O$_3$): C, 53.58; H, 4.27; N, 15.62; Cl, 15.82. Found: C, 53.74; H, 4.23; N, 15.55; Cl, 15.68.

4. Synthesis of Compounds 6a-n and 6p:

A mixture of the corresponding guanidine 11 (see Table 2, above) (1.0 eq.) and dione 8 (1.1-1.5 eq.) in anhydrous CHCl$_3$ was heated in a sealed tube at 100° C. for 48-60 hours. The solvent was removed under reduced pressure. The residue was purified via a silica gel column chromatography. CHCl$_3$/EtOAc was used as eluents for the purification of compounds 6a-n and 6p. Compounds were further purified by recrystallization from EtOAc to give compounds 6a-n and 6p in 20-40% yields. Physical properties of the final products are listed in Table 4. NMR, LC/MS and elemental analysis results are listed below:

TABLE 4

Imidazolidinedione Derivatives Represented by Structures 6

| No. | WR# | R | Yield (%) | Mp(° C.) | MS (m/z) |
|-----|--------|-----------------------------|-----|-----|--------------|
| 6a  | 308334 | —CH$_3$                     | 40  | 229 | 355 (M$^+$)  |
| 6b  | 308241 | —CH$_2$CH$_3$               | 26  | 217 | 369 (M$^+$)  |
| 6c  | 301855 | —CH$_2$(CH$_3$)$_2$         | 20  | 191 | 383 (M$^+$)  |
| 6d  | 308274 | —C(CH$_3$)$_3$              | 26  | 243 | 397 (M$^+$)  |
| 6e  | 308271 | —CH$_2$C(CH$_3$)$_3$        | 37  | 203 | 411 (M$^+$)  |
| 6f  | 308661 | —C$_6$H$_5$                 | 25  | 189 | 417 (M$^+$)  |
| 6g  | 308332 | —CH$_2$C$_6$H$_5$           | 34  | 190 | 431 (M$^+$)  |
| 6h  | 308629 | —(CH$_2$)$_5$CH$_3$         | 21  | 147 | 426 (M$^+$)  |
| 6i  | 308596 | 2-Adamantyl                 | 32  | 251 | 475          |
| 6j  | 308757 | —(CH$_2$)$_2$—NMe$_2$       | 18  | 198 | 413 (M + 1)  |
| 6k  | 308660 | —(CH$_2$)$_2$N(CH$_2$CH$_3$)$_2$ | 17 | 139 | 441 (M$^+$) |
| 6l  | 308758 | —(CH$_2$)$_2$—N(pyrrolidine) | 16 | 196 | 439 (M + 1) |
| 6m  | 308759 | —(CH$_2$)$_3$NMe$_2$        | 31  | 110 | 427 (M + 1)  |
| 6n  |        | —(CH$_2$)$_4$—N(pyrrolidine) | 23 | 80  | 467 (M$^+$) |
| 6p  | 308664 | —(CH$_2$)$_6$NH-t-Boc*      | 39  | 142 | 541 (M + 1)  |

*t-Boc = tert-Butoxycarbonyl-

N-Methyl Derivatives of Compound 1 (6a): $^1$H NMR (CDCl$_3$) 1.48 (d, J=6.9 Hz, 6H), 3.10 (s, 3H), 4.58 (q, J=6.9 Hz, 1H), 7.14 (br d, J=8.6 Hz, 1H), 7.40 (s, 1H), 7.56 (d, J=8.6 Hz, 1H). Anal. calcd for (C$_{14}$H$_{15}$Cl$_2$N$_5$O$_2$): C, 47.21; H, 4.24; Cl, 19.91; N, 19.66. Found: C, 47.28; H, 4.22; Cl, 20.07; N, 19.53. MS (m/z): 355 (M$^+$)

N-Ethyl Derivatives of Compound 1 (6b): $^1$H NMR (CDCl$_3$): δ 10.52 (br s, 1H), 7.55 (d, J=8.56 Hz, 1H), 7.39 (br s, 1H), 7.12 (d, J=8.74, Hz, 1H), 4.55 (m, 1H), 3.57 (q, J=7.35 Hz, 2H), 1.47 (d, J=6.90 Hz, 6H), 1.24 (t, J=7.00 Hz, 3H); $^{13}$C NMR (DMSO-d$_6$): 158.30, 155.59, 131.79, 131.34, 126.96, 124.18, 119.90, 47.36, 39.05, 19.23, 13.60; MS (m/z) 369.00 (M$^+$); Anal. calcd for (C$_{15}$H$_{17}$Cl$_2$N$_5$O$_2$): C, 48.66; H, 4.63; Cl, 19.15; N, 18.92. Found: C, 48.48; H, 4.47; Cl, 19.25; N, 18.72.

N-Isopropyl Derivatives of Compound 1 (6c): $^1$H NMR (CDCl$_3$) δ 1.27 (d, J=6.6 Hz, 6H), 1.47 (d, J=6.9 Hz, 6H), 4.39

(q, J=6 Hz, 1H), 4.53 (q, J=6.9 Hz, 1H), 7.11 (dd, J=8.4 Hz, and 2.5 Hz, 1H), 7.38 (d, J=2.5 Hz, 1H), 7.57 (d, J=8.4 Hz, 1H); $^{13}$C NMR (CDCl$_3$): 20.2, 22.7, 44.6, 45.1, 125.1, 127.8, 132.0, 132.4, 134.1, 134.3, 157.6, 161.1, 169.9, 171.9. Anal. calcd for (C$_{16}$H$_{19}$Cl$_2$N$_5$O$_2$): C, 50.01; H, 4.98; N, 18.23; Cl, 18.45. Found: C, 49.86; H, 5.05; N, 17.99; Cl, 18.58. MS (m/z): 383 (M$^+$).

N-t-Butyl Derivatives of Compound 1 (6d): $^1$H NMR (CDCl$_3$): δ 7.56 (d, J=8.51 Hz, 1H), 7.37 (br s, 1H), 7.10 (dd, J=8.47 and 2.20 Hz, 1H), 5.19 (br s, 1H), 4.57 (m, 1H), 1.51 (d, J=6.92 Hz, 6H) 1.42 (s, 9H); $^{13}$C NMR (CDCl$_3$); 171.22, 169.94, 161.15, 158.10, 134.34, 131.91, 127.61, 124.84, 54.13, 44.87, 29.59, 19.81. MS (m/z): 397.00 (M$^+$). Anal.: calcd for (C$_{17}$H$_{21}$Cl$_2$N$_5$O$_2$): C, 51.27; H, 5.31; Cl, 17.80; N, 17.58. Found: C, 51.30; H, 5.32; Cl, 17.99; N, 17.29.

N-Neopentyl Derivatives of Compound 1 (6e): Mp: 203° C. (dec), Major tautomer $^1$H NMR (CDCl$_3$): δ 0.94 (s, 9H), 1.48 (d, J=6.5 Hz, 6H), 3.38 (br d, J=5.8 Hz, 2H), 4.55 (q, J=8.5 Hz, 1H), 7.14 (br d, J=8.3 Hz, 1H), 7.41 (br s, 1H), 7.58 (br d, J=8.3 Hz, 1H); Minor tautomer $^1$H NMR (CDCl$_3$): δ 1.07 (s, 9H), 1.30 (d, J=7.1 Hz, 6H), 3.23 (br s, 2H), 4.34 (q, J=7.1 Hz, 1H), 7.20 (br d, J=8.3 Hz, 1H), 7.55 (br s, 1H), 7.64 (br s, 1H). Major tautomer: $^{13}$C NMR (CDCl$_3$): δ 20.1, 27.4, 31.7, 44.7, 54.1, 124.4, 127.5, 127.5, 129.9, 131.9, 136.4, 157.8, 161.6, 170.7, 171.5; Minor tautomer $^{13}$C NMR (CDCl$_3$): δ. 19.8, 27.4, 32.6, 44.6, 53.3, 125.1, 127.8, 129.4, 131.8, 134.1, 159.2, 161.5, 170.3, and 171.5. Anal: calcd for (C$_{18}$H$_{23}$Cl$_2$N$_5$O$_2$): C, 52.43; H, 5.62; Cl, 17.20; N, 16.99. Found: C, 52.66; H, 5.71; Cl, 16.91; N, 16.81. MS (m/z): 411 (M$^+$).

N-Phenyl Derivatives of Compound 1 (6f): $^1$H NMR (CDCl$_3$): δ 1.34 (d, J=6.9 Hz, 6H), 4.40 (q, J=6.97 Hz, 1H), 7.10 (br d, J=8.1 Hz, 1H), 7.32-7.60 (m, 7H). MS (m/z): 417 (M$^+$). Anal. calcd for (C$_{20}$H$_{19}$Cl$_2$N$_5$O$_2$): C, 55.57; H, 4.43; Cl, 16.40; N, 16.20. Found: C, 55.38; H, 4.43; Cl, 16.52; N, 16.01.

N-Benzyl Derivatives of Compound 1 (6g): $^1$H NMR (CDCl$_3$) δ 1.40 (d, J=6.8 Hz, 6H), 4.52 (q, J=6.8 Hz, 1H), 4.74 (br d, J=5.4 Hz, 2H), 5.97 (br s, 1H), 7.13 (br d, J=8.5 Hz, 1H), 7.25-7.40 (m, 6H), 7.53 (d, J=8.5 Hz, 1H). Anal. calcd for (C$_{20}$H$_{19}$Cl$_2$N$_5$O$_2$): C, 55.57; H, 4.43; Cl, 16.40; N, 16.20. Found: C, 55.38; H, 4.43; Cl, 16.52; N, 16.01. MS (m/z): 431 (M$^+$).

N-Hexyl Derivatives of Compound 1 (6h): $^1$H NMR (CDCl$_3$) δ 0.86-0.91 (m, 3H), 1.30 (br s, 6H), 1.47 (d, J=6.9 Hz, 6H), 1.58-1.63 (m, 2H), 3.49-3.54 (m, 2H), 4.55 (q, J=6.7 Hz, 1H), 7.12 (dd, J=8.5 Hz and 2.2 Hz, 1H), 7.39 (d, J=2.2 Hz, 1H), 7.54 (d, J=8.5 Hz, 1H). $^{13}$C NMR (CDCl$_3$) major tautomer: δ 14.0, 20.1, 22.5, 26.4, 29.6, 31.4, 42.7, 44.7, 124.5, 127.6, 129.9, 131.6, 133.8, 136.4, 157.4, 161.5, 170.4, 170.9; minor tautomer: δ 14.0, 19.8, 22.5, 26.5, 28.6, 31.3, 42.5, 44.7, 125.1, 127.6, 129.4, 131.9, 134.3, 136.4, 158.6, 161.5, 170.4, 171.4. Anal: calcd for (C$_{19}$H$_{25}$Cl$_2$N$_5$O$_2$): C, 53.53; H, 5.91; N, 16.43; Cl, 16.63. Found: C, 53.47; H, 5.84; N, 16.27; Cl, 16.74. MS (m/z): 426 (M+1)$^+$.

N-2-Adamantyl Derivatives of Compound 1 (6i): $^1$H NMR (DMSO-d$_6$ with D$_2$O): δ 1.17 (d, J=6.7 Hz, 6H), 1.64-1.74 (m, 4H), 1.87-2.03 (m, 10H), 4.07 (s, 1H), 4.17 (q, J=6.7 Hz, 1H), 7.34 (br d, J=8.6 Hz, 1H), 7.66 (br d, J=8.6 Hz, 1H), 7.74 (s, 1H). $^{13}$C NMR (CDCl$_3$) major tautomer: δ 20.3, 26.7, 31.9, 36.8, 37.0, 44.6, 56.5, 124.4, 127.3, 129.9, 132.2, 134.0, 136.3, 157.3, 161.1, 169.9, 171.6; minor tautomer: δ 19.8, 26.6, 31.9, 36.6, 37.1, 44.5, 56.8, 124.5, 127.7, 129.5, 132.5, 134.6, 136.3, 156.1, 161.5, 170.7, 172.2. mp: 251.2-253.8° C. Anal: calcd for C$_{23}$H$_{27}$Cl$_2$N$_5$O$_2$: C, 57.99; H, 5.71; N, 14.70; Cl, 14.88. Found: C, 57.00; H, 5.62; N, 14.40; Cl, 15.94. MS (m/z) 475 (M$^+$).

N-[2-(N',N'-dimethylaminoethyl] Derivatives of Compound 1 (6j): $^1$H NMR (CDCl$_3$): δ 10.61 (br s, 1H), 7.58 (d, J=2.37 Hz, 1H), 7.40 (d, J=8.59 Hz, 1H), 6.95 (dd, J=8.59 Hz and 2.40 Hz, 1H), 4.39 (m, 1H), 3.51 (br s, 2H), 2.78 (t, J=4.10 Hz, 2H), 2.46 (s, 6H), 1.34 (d, J=6.94 Hz, 6H); $^{13}$C NMR (CDCl$_3$): δ 171.73, 170.59, 161.34, 159.98, 137.50, 132.57, 130.34, 128.45, 125.41, 121.91, 60.65, 44.96, 44.61, 41.66, 19.91. Anal. calcd for (C$_{17}$H$_{22}$Cl$_2$N$_6$O$_2$): C, 49.40; H, 5.37; Cl, 17.16; N, 20.33. Found: C, 49.60; H, 5.53; Cl, 17.03; N, 19.97. LC/MS (m/z): 413 (M+1)$^+$.

N-[2-(N',N'-diethylaminoethyl] Derivatives of Compound 1 (6k): $^1$H NMR (CDCl$_3$): δ 10.60 (br s, 1H, NH), 7.52 (d, J=2.42 Hz, 1H), 7.40 (d, J=8.57 Hz, 1H), 6.97 (dd, J=8.55 Hz and 2.40 Hz, 1H), 4.36 (m, 1H), 3.52 (br s, 2H), 2.78 (t, J=3.86 Hz, 2H), 2.73 (q, J=7.8 Hz, 4H), 1.32 (d, J=6.95 Hz, 6H), 1.10 (t, J=7.20 Hz, 6H). $^{13}$C NMR (CDCl$_3$): δ 171.89, 170.62, 161.30, 160.40, 137.07, 132.58, 130.29, 128.75, 126.14, 122.49, 55.17, 47.25, 44.54, 42.68, 19.91, 10.96. Anal. calcd for (C$_{19}$H$_{26}$Cl$_2$N$_6$O$_2$): C, 51.71; H, 5.94; Cl, 16.07; N, 19.04. Found: C, 51.69; H, 5.95; Cl, 16.19; N, 18.91. LC/MS (m/z): 441 (M+1)$^+$.

N-[2-(Pyrrolidino)ethyl] Derivatives of Compound 1 (6l): $^1$H NMR (CDCl$_3$): δ 1.33 (d, 6.9 Hz, 6H), 1.91 (br s, 4H), 2.85 (br s, 4H), 2.92-2.95 (m, 2H), 3.55 (br s, 2H), 4.38 (q, J=6.9 Hz, 1H), 6.98 (d, J=8.6 Hz, 1H), 7.41 (d, J=8.6 Hz, 1H), 7.49 (s, 1H). $^{13}$C NMR (CDCl$_3$): δ 19.7, 23.6, 41.9, 44.3, 53.6, 57.0, 122.3, 125.7, 128.1, 130.1, 132.2, 138.2, 159.6, 161.3, 170.4. Anal. calcd for C$_{19}$H$_{24}$Cl$_2$N$_6$O$_2$: C, 51.94; H, 5.51; N, 19.13; Cl, 16.14. Found: C, 51.78; H, 5.59; N, 18.84; Cl, 15.89. LC-MS (m/z): 439 (M+1)$^+$.

N-(3-(N',N'-dimethylaminopropyl)] Derivatives of Compound 1 (6m): $^1$H NMR (CDCl$_3$): major tautomer: δ 1.33 (d, J=6.9 Hz, 6H), 1.70 (br s, 2H), 1.89 (s, 6H), 2.41-2.44 (m, 2H), 3.64 (br s, 2H), 4.37 (q, J=6.9 Hz, 1H), 7.06 (dd, J=8.6 Hz and 2.4 Hz, 1H), 7.40 (d, J=2.6 Hz, 1H), 7.42 (d, J=8.6 Hz, 1H); minor tautomer: δ 1.47 (d, J=6.9 Hz, 6H), 1.89 (br s, 2H), 2.22 (s, 6H), 2.47-2.52 (m, 2H), 3.66-3.68 (m, 2H), 4.56 (q, J=6.9 Hz, 1H), 7.13 (dd, J=8.5 Hz and 2.6 Hz, 1H), 7.54 (d, J=8.5 Hz, 1H), 7.64 (d, J=2.8 Hz, 1H). Anal calcd for C$_{18}$H$_{24}$Cl$_2$N$_6$O$_2$: C, 50.59; H, 5.66; N, 19.67; Cl, 16.59. Found: C, 50.46; H, 5.59, 5.66; N, 19.76; Cl, 16.48. LC-MS (m/z): 426 (M)$^+$, 427 (M+1)$^+$.

N-[4-(Pyrrolidino)butyl] Derivatives of Compound 1 (6n): $^1$H NMR (CDCl$_3$): δ 7.48 (d, J=8.76 Hz, 1H), 7.39 (s, 1H), 7.09 (d, J=7.56 Hz and 1H), 4.53 (m, 1H)*, 3.53 (br s, 2H)*, 2.61 (br s, 2H)*, 2.34 (br s, 4H)*, 1.69 (br s, 4H)*, 1.58 (br s, 4H), 1.45 (d, J=6.63 Hz, 6H)*. $^{13}$C NMR (CDCl$_3$): δ 171.08, 170.46, 168.55, 161.53, 158.49*, 139.30, 133.59*, 131.44*, 126.29*, 124.00*, 55.85*, 54.06, 44.49, 42.67*, 27.58*, 26.27*, 23.31*, 20.13*. Anal calcd for (C$_{21}$H$_{28}$Cl$_2$N$_6$O$_2$): C, 53.96; H, 6.04; Cl, 15.17; N, 17.98. Found: C, 53.43; H, 6.03; Cl, 14.93; N, 17.80. LCMS (m/z): 467 (M+1)$^+$.

N-(6-tert-Butoxycarbonylaminohexyl-) Derivatives of Compound 1 (6p): $^1$H NMR (CDCl$_3$): δ 1.30-1.80 (m, 8H), 1.36 (s, 9H), 1.47 (d, J=6.9 Hz, 6H), 3.06-3.19 (m, 2H), 3.43-3.55 (m, 2H), 4.55 (q, J=6.9 Hz, 1H), 7.13 (dd, J=2.2 Hz and 8.5 Hz, 1H), 7.41 (d, J=2.2 Hz, 1H), 7.52 (d, J=8.5 Hz, 1H). $^{13}$C NMR (CDCl$_3$): major tautomer: δ 20.0, 25.5, 26.0, 28.2, 29.3, 29.9, 39.6, 42.2, 44.5, 79.0, 124.4, 127.5, 129.8, 131.4, 133.6, 136.3, 156.0, 161.4, 170.7, 171.2; minor tautomer: δ 19.7, 25.4, 26.3, 28.3, 29.7, 29.9, 40.2, 41.8, 44.5, 125.2, 127.7, 129.3, 131.8, 134.2, 136.3, 157.4, 158.3, 170.2, 171.2. Anal: calcd for C$_{24}$H$_{34}$Cl$_2$N$_6$O$_4$: C, 53.24; H, 6.33; Cl, 13.10; N, 15.52. Found: C, 53.23; H, 6.40; Cl, 13.05; N, 15.47. LC/MS (m/z): 540 (M)$^+$, 541 (M+1)$^+$.

Compounds 7a-c were synthesized according to the following general procedure. Carboxamides 7a-c were prepared by acylation of compound 1 as exemplified by the synthesis of carboxamide 7a (Scheme 2). To a suspension of compound 1 (5 g, 14.6 mmol) in 100 mL of $CHCl_3$ was added with stirring $Et_3N$ (4.1 mL, 2 equiv) and DMAP (179 mg, 0.1 equiv). The reaction mixture was cooled to 0° C. with an ice bath and 2-ethylbutyryl chloride (3 mL, 1.5 equiv) was added dropwise. The reaction mixture was stirred at room temperature overnight, washed with water, and the chloroform layer was dried over $Na_2SO_4$, and evaporated to dryness under the reduced pressure. The residue was applied to a silica gel flash column and eluted with 2% $EtOAc/CHCl_3$ to give a white solid which was recrystallized from $Hexane/CHCl_3$, to obtain the desired compound 7a as light yellow solid (2.6 g, 40%), m.p. 206.5-208.4° C., $^1H$ NMR ($CDCl_3$): δ 13.8 (s, 1H), 12.0 (s, 1H), 7.92 (d, J=2.4 Hz, 1H), 7.53 (d, J=8.6 Hz, 1H), 7.25 (dd, J=8.6 Hz, and 2.4 Hz, 1H), 4.48 (m, 1H), 2.43 (m, 1H), 1.76 (m, 4H), 1.44 (d, J=6.9 Hz, 6H), 1.01 (t, J=7.3 Hz, 6H); MS (m/z) 440 $(M+1)^+$. Anal: calcd for $(C_{19}H_{23}N_5O_3Cl_2.3/4H_2O)$: C, 50.28; H, 5.44; N, 15.43. Found: C, 50.27; H, 5.11; N, 15.22.

Compound 7b was prepared according to the same procedure as described for the preparation of compound 7a, but by treating compound 1 with isobutyryl chloride to give 26% yield of pale yellow crystals. m.p. 188-190° C. $^1H$ NMR ($CDCl_3$): δ 7.86 (d, J=2.5 Hz, 1H), 7.51 (d, J=8.6 Hz, 1H), 7.22 (dd, J=8.6 Hz and 2.5 Hz, 1H), 4.45 (m, 1H), 2.77 (m, 1H), 1.39 (d, J=6.9 Hz, 6H), 1.33 (d, J=6.9 Hz, 6H). MS (m/z): 412 $(M+1)^+$, 342. Anal: $(C_{17}H_{19}N_5O_3Cl_2)$ Calcd: C, 49.53; H, 4.65; N, 16.99. Found: C, 49.70; H, 4.56; N, 16.99.

Compound 7c was prepared using trimethylacetic anhydride as acylating agent to yield 23% of the desired product after purification, mp 183.3-190.7° C. $^1H$ NMR ($CDCl_3$): δ 7.90 (d, J=2.5 Hz, 1H), 7.53 (d, J=8.6 Hz, 1H), 7.25 (dd, J=8.6 Hz and 2.5 Hz, 1H), 4.48 (m, 1H), 1.42 (d, J=7.1 Hz, 6H), 1.40 (s, 9H). MS (m/z) 426 $(M+1)^+$, and 342. Anal: $(C_{18}H_{21}N_5O_3Cl_2)$ Calcd: C, 50.71; H, 4.97; N, 16.43. Found: C, 50.41; H, 4.99; N, 16.31.

Pharmaceutical Compositions and Methods of Treatment

The compounds within the scope of the present embodiments can be used to treat, prevent or inhibit all types of malaria, for example, malaria caused by *P. falciparum, P. vivax, P. ovale* or *P. malariae*. Of particular interest, however, is the treatment or prevention of malaria caused by *P. vivax*.

The compounds of the embodiments described herein include pharmaceutical compositions, pharmaceutically acceptable salts, multimeric forms, prodrugs, active metabolites, precursors and salts of such metabolites of the compounds.

The term "pharmaceutically acceptable salts" refers to salt forms that are pharmacologically acceptable and substantially non-toxic to the subject being treated with a compound described herein. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of compounds described herein. Such "multimers" can be made by linking or placing multiple copies of an active compound in close proximity to each other, e.g., using a scaffolding provided by a carrier moiety. Multimers of various dimensions (i.e., bearing varying numbers of copies of an active compound) can be tested to arrive at a multimer of optimum size with respect to receptor binding. Provision of such multivalent forms of active receptor-binding compounds with optimal spacing between the receptor-binding moieties can enhance receptor binding. See, for example, Lee et al., (1984) Biochem. 23:4255. The artisan can control the multivalency and spacing by selection of a suitable carrier moiety or linker units. Useful moieties include molecular supports comprising a multiplicity of functional groups that can be reacted with functional groups associated with active compounds. A variety of carrier moieties can be used to build highly active multimers, including proteins such as BSA (bovine serum albumin) or peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, can be selected to obtain stable linkages to compounds described herein, optimal spacing between the immobilized compounds, and optimal biological properties.

"A pharmaceutically acceptable prodrug" is a compound that can be converted under physiological conditions or by solvolysis to the specified compound or to a pharmaceutically acceptable salt of such compound. A "pharmaceutically active metabolite" is intended to mean a pharmacologically active product produced through metabolism in the body of a specified compound or salt thereof. Prodrugs and active metabolites of a compound can be identified using routine techniques known in the art See, e.g., Bertolini, G. et al., (1997) J. Med. Chem. 40:2011 2016; Shan, D. et al., J. Pharm. Sci., 86(7):765 767; Bagshawe K., (1995) Drug Dev. Res. 34:220 230; Bodor, N., (1984) Advances in Drug Res. 13:224 331; Bundgaard, H., Design of Prodrugs (Elsevier Press, 1985); and Larsen, I. K., Design and Application of Prodrugs, Drug Design and Development (Krogsgaard-Larsen et al., eds., Harwood Academic Publishers, 1991).

If the compound of an embodiment is a base, the desired pharmaceutically acceptable salt can be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of an embodiment is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound and salts can exist in different crystal or polymorphic forms, all of which are intended to be within the scope of the embodiments described herein and specified structural formulas.

The compounds described herein can be useful in the treatment malaria and diseases and disorders associated with malaria or a *Plasmodium* parasite.

The antimalarial activity of compounds can be measured by any of the methods available to those skilled in the art, including in vitro and in vivo assays. Examples of suitable assays for activity measurements are provided herein. Properties of the compounds described herein can be assessed, for example, by using one or more of the assays set out in the Examples below. Other pharmacological methods can also be used to determine the efficacy of the compounds as antimalarial agents.

The compounds described herein can be used in combination with or as a substitution for treatments of the above conditions. For example, the compounds described herein can also be used alone or combination with antimalarial agents known in the art. The compounds described herein can be used alone or in combination with supplementary active compounds including, for example, antibiotics, antiprotozoal agents, and analgesics known in the art. Supplementary active compounds include, for example, proquanil, atovaquone, primaquine, tafenoquine, mefloquine, artemisinin derivatives, and sulfa-drugs.

The specification for dosage unit forms are typically dictated by and directly dependent on the unique characteristics of the active compound and the particular therapeutic effect to be achieved, and the limitations inherent in the art of compounding such an active compound for the treatment of individuals.

A compound described herein can be administered in a therapeutically effective amount to a mammal such as a human. Therapeutically effective amounts of the compounds described herein can be used to treat, modulate, attenuate, reverse, or affect malaria in a mammal. An "effective amount" is intended to mean that amount of an agent that is sufficient to treat, prevent, or inhibit malaria or a disease or disorder associated with malaria. In some preferred embodiments, malaria or the disease or disorder associated with malaria is caused by a *Plasmodium* parasite, preferably, *P. falciparum, P. vivax, P. ovale,* or *P. malariae*.

Thus, e.g., a "therapeutically effective amount" of a compound described herein, a prodrug, an active metabolite, or a salt thereof, is a quantity sufficient to, when administered to a mammal, treat, prevent, or inhibit malaria or a disease or disorder associated with malaria or a *Plasmodium* parasite. The amount of a given compound that will correspond to such an amount will vary depending upon factors such as the given drug or compound, the pharmaceutical formulation and route of administration, the type of disease or disorder, the identity of the subject or host being treated, and the like, but can nevertheless be routinely determined by one skilled in the art. Also, as used herein, a "therapeutically effective amount" of a compound is an amount which prevents, inhibits, suppresses, or reduces malaria (as determined by clinical symptoms or the amount of *Plasmodium* organisms) in a subject as compared to a control. As defined herein, a therapeutically effective amount of a compound can be readily determined by one of ordinary skill by routine methods known in the art.

For example, a therapeutically effective amount of a compound described herein typically ranges from about 0.1 to about 1,000 mg/kg body weight, preferably about 0.1 to about 500 mg/kg body weight, and more preferably about 0.1 to about 100 mg/kg body weight. The skilled artisan will appreciate that certain factors can influence the dosage required to effectively treat a subject, including but not limited to the severity of the disease or disorder, previous treatments, the general health and/or age of the subject, and other diseases present.

Moreover, treatment of a subject with a therapeutically effective amount of a compound described herein can consist of a single administration, or alternatively comprise a series of applications. For example, a subject can be treated with a compound at least once. However, the subject can treated with the compound from about one time per week to about once daily for a given treatment period. The length of the treatment period will depend on a variety of factors such as the severity of inflammation, the concentration and activity of the compounds, or a combination thereof. It will also be appreciated that the effective dosage of the compound used for treatment can increase or decrease over the course of a particular treatment. Changes in dosage can result and become apparent by standard diagnostic assays known in the art. In some instances chronic administration can be required. The compounds described herein can be administered before, during, after, or a combination thereof exposure to malaria or a *Plasmodium* parasite.

The pharmaceutical formulations described herein comprise at least one compound of the present embodiments and can be prepared in a unit-dosage form appropriate for the desired mode of administration. Pharmaceutical formulations can be administered for therapy by any suitable route. In preferred embodiments, the route of administration is oral, parenteral (including subcutaneous, intramuscular, intravenous and intradermal), transdermal, nasal, and rectal (e.g., by suppository). It will be appreciated that the preferred route will vary with the condition and age of the recipient, the nature of the condition to be treated, and the chosen compound.

It will be appreciated that the actual dosages of the compounds used in pharmaceutical formulations will vary according to the particular complex being used, the particular composition formulated, the mode of administration, and the particular site, host, and disease being treated. Optimal dosages for a given set of conditions can be ascertained by those skilled in the art using conventional dosage determination tests in view of the experimental data for a given compound. Administration of prodrugs can be dosed at weight levels that are chemically equivalent to the weight levels of the fully active forms.

The compounds described herein can be incorporated into pharmaceutical formulations suitable for administration. Pharmaceutical formulations typically comprise a therapeutically effective amount of at least one compound described herein, and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed can be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art.

Except insofar as any conventional media or agent is incompatible with the active compound, use thereof in the formulation is contemplated. Supplementary active compounds can also be incorporated into the formulations. Supplementary active compounds include antimalarials, antibacterials, antiprotozoal agents, anti-inflammatory agents, and other compounds commonly used to treat diseases and disorders related to cell proliferation, inflammation, and bacterial, protozoal, and fungal infections. Supplementary active compounds include, for example:

Antimalarials such as chloroquine, quinine, mefloquine, amodiaquin, primaquine, pyrimethamine, sulfonamides, sulfones, dihydrofolate reductase inhibitors, tetrandine, derivatives thereof, and the like. As used herein, the term "antimalarial" refers to compounds that show activity against *Plasmodium* parasites using assays known in the art.

Antibiotics such as penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, ceffuroxime, ceftriaxone, vancomycin, gentamicin, amikacin, metronidazole, chloramphenicol, nitrofurantoin, co-trimoxazole, rifampicin, isoniazid, pyrazinamide, and the like;

Antiprotozoal agents include chloroquine, doxycycline, mefloquine, metronidazole, eplomithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like; and Anti-inflammatory agents include steroids such as predinsolone, corticosteroid, and the like.

A pharmaceutical formulation is typically formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier can vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent can be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from about 0% to about 60% of the total volume.

The pharmaceutical formulation can also be in the form of a solution of a salt form of the active ingredient in an appropriate aqueous vehicle such as water or isotonic saline or dextrose solution.

Pharmaceutical formulations can be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical formulations can be formulated in a conventional manner using one or more physiologically acceptable carriers, which can be selected from excipients and auxiliaries that facilitate processing of the active compounds into preparations which can be used pharmaceutically.

Proper formulation is dependent upon the route of administration chosen. For injection, the agents of the embodiments described herein can be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds described herein can be formulated readily by combining with pharmaceutically acceptable carriers known in the art. Such carriers enable compounds to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents can be added, such as crosslinked polyvinyl pyrrolidone, agar, or alginic acid or a salt thereof such as sodium alginate.

Dragee cores are provided with suitable coatings. For this purpose, concentrated sugar solutions can be used, which can optionally comprise gum horoi, polyvinyl pyrrolidone, Carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compounds and agents.

Pharmaceutical formulations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the formulations can take the form of tablets or lozenges formulated in conventional manner.

Oral formulations generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral formulations can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds described herein can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of gelatin for use in an inhaler or insufflator and the like can be formulated comprising a powder mix of the compound and a suitable powder base such as lactose or starch.

The compounds described herein can be formulated for parenteral administration by injection, e.g., by bolus injection or continuous infusion. Formulations for injection can be presented in unit-dosage form, e.g., in ampoules or in multi-dose containers, with an added preservative. The formulations can take such forms as suspensions, solutions or emulsions in oily or aqueous vehicles, and can comprise formulatory agents such as suspending, stabilizing and/or dispersing agents.

Pharmaceutical formulations suitable for injectable use include sterile aqueous solutions (where water soluble) or dispersions and sterile powders for the extemporaneous preparation of sterile injectable solutions or dispersion. Aqueous injection suspensions can comprise substances which increase the viscosity of the suspension, such as sodium carboxymethyl cellulose, sorbitol, or dextran. Optionally, the suspension can also comprise suitable stabilizers or agents which increase the solubility of the compounds to allow for the preparation of highly concentrated solutions. Additionally, suspensions of the active agents can be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid horoidsene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the formulation. Prolonged absorption of the injectable compositions can be brought about by including in the formulation an agent which delays absorption, for example, aluminum monostearate and gelatin.

Sterile injectable solutions can be prepared by incorporating a therapeutically effective amount of at least one compound described herein in an appropriate solvent with one or a combination of ingredients enumerated above, as required, followed by filtered sterilization. Generally, dispersions are prepared by incorporating a compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

Alternatively, compounds described herein can be in powder form for constitution with a suitable vehicle, e.g., sterile pyrogen-free water, before use. Compounds can also be formulated in rectal compositions such as suppositories or retention enemas, e.g., comprising conventional suppository bases such as cocoa butter or other glycerides.

In addition to the formulations described above, compounds can also be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system can be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied, for example: other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can be substituted for dextrose.

Alternatively, other delivery systems for hydrophobic pharmaceutical formulations can be employed. Liposomes and emulsions are known examples of delivery vehicles or carriers for hydrophobic drugs. Certain organic solvents such as dimethylsulfoxide also can be employed, although usually at the cost of greater toxicity. Additionally, the compounds can be delivered using a sustained-release system, such as semipermeable matrices of solid hydrophobic polymers comprising the therapeutic agent. Various sustained-release materials have been established and are known by those skilled in the art. Sustained-release capsules can, depending on their chemical nature, release the compounds for a few weeks up to over 100 days. Depending on the chemical nature and the biological stability of the therapeutic reagent, additional strategies for protein stabilization can be employed.

The pharmaceutical formulations also can comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds described herein can be provided as salts with pharmaceutically compatible counter ions. Pharmaceutically compatible salts can be formed with many acids, including hydrochloric, sulfuric, acetic, lactic, tartaric, malic, succinic, and the like. Salts tend to be more soluble in aqueous or other protonic solvents than are the corresponding free-base forms.

In some embodiments, compounds described herein are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral formulations in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for dosage unit forms are typically dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the embodiments described herein, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The inhibitors of the preferred embodiments can be provided to an administering physician or other health care professional in the form of a kit. The kit is a package which houses a container which contains one or more compounds described herein in a suitable pharmaceutical composition, and instructions for administering the pharmaceutical composition to a subject. The kit can optionally also contain one or more additional therapeutic agents. For example, a kit containing one or more compositions comprising compound(s) of the present embodiments in combination with one or more additional antimalarial, antibacterial, and/or anti-inflammatory agents can be provided, or separate pharmaceutical compositions containing a compound of the preferred embodiments and additional therapeutic agents can be provided. The kit can also contain separate doses of a compound of the present embodiments for serial or sequential administration. The kit can optionally contain one or more diagnostic tools and instructions for use. For example, the kit can contain reagents for assaying whether the subject is in need of the compound, e.g. assay for whether the subject has malaria or has been exposed to a *Plasmodium* parasite. The kit can contain suitable delivery devices, e.g., syringes, and the like, along with instructions for administering the compound(s) and any other therapeutic agent. The kit can optionally contain instructions for storage, reconstitution (if applicable), and administration of any or all therapeutic agents included. The kits can include a plurality of containers reflecting the number of administrations to be given to a subject.

The following Examples are intended to illustrate but not to limit the invention. In the following Examples, the compounds having the structural formulas in the above-referenced Schemes are referenced.

EXAMPLES

Example 1

New compounds were assessed for their causal prophylactic activity in two different exoerythrocytic (EE) mouse models using sporozoites of either *P. berghei* or *P. yoelii*. The procedures have been previously described (see, for example, Q. Zhang et al., *J. Med. Chem.* 48 (20): 6472-6481 (2005)). Briefly, each compound was ground with a mortar and pestle and suspended in hydroxyethylcellulose and Tween 80 for compounds to be administered PO and those given SC were suspended in peanut oil. Each compound was prepared at different dose levels. Compounds were administered either PO or SC to mice once a day for three consecutive days, to mice on the day before, 4 hours before, and the day after being inoculated intraperitoneally with *P. yoelii* sporozoites or *P. berghei* sporozoites intravenously. Whole body weights were taken on Day 0 and Day 6 then approximately twice a week for 31 days. A blood film was taken on Day 5 and then approximately twice a week for 31 days. Mice losing greater than about 20% of their body weight were sacrificed. A compound was considered active if only low levels of parasites were found (less than about 10%) in blood films taken on Day 5 or any biweekly for 31 days. Mice alive on Day 31 with no parasites found in any blood films were considered protected.

Table 5 summarizes the test results of a number of new compounds described herein. The results indicated that the new compounds were much more active in mice infected with sporozoites of *P. yoelii* than with *P. berghei* (see Table 5). Note, for example, compounds 6e, 6f and 6i. In addition, compounds 6e, 6f and 6i displayed enhanced protection compared to control compound 3.

TABLE 5

Causal Prophylactic Activity against EE *P. berghei* and *P. yoelli*

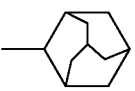

| Compounds | R | Dose/day (mg/kg) | # Days Treated | P. berghei # Mice Protected/ # Mice Used | P. yoelli # Mice Protected/ # Mice Used |
|---|---|---|---|---|---|
| 3 (Control) | —COOC(CH$_3$)$_3$ | 160 | 3 | 4/10 | 4/5 |
| | | 40 | 3 | 2/10 | 2/5 |
| | | 10 | 3 | — | 3/5 |
| 5e | —OCH$_2$C$_6$H$_5$ | 160 | 3 | 0/5 | — |
| | | 40 | 3 | 0/5 | — |
| | | 10 | 3 | — | — |
| 6c | —CH(CH$_3$)$_2$ | 160 | 3 | 1/5 | — |
| | | 40 | 3 | 0/5 | — |

TABLE 5-continued

Causal Prophylactic Activity against EE *P. berghei* and *P. voelli*

| Compounds | R | Dose/day (mg/kg) | # Days Treated | P. berghei # Mice Protected/ # Mice Used | P. yoelli # Mice Protected/ # Mice Used |
|---|---|---|---|---|---|
| | | 10 | 3 | — | — |
| 6e | —CH$_2$C(CH$_3$)$_3$ | 160 | 3 | 1/5 | 5/5 |
| | | 40 | 3 | 0/5 | 5/5 |
| | | 10 | 3 | — | 5/5 |
| 6f | —C$_6$H$_5$ | 160 | 3 | 0/5 | 5/5 |
| | | 40 | 3 | 0/5 | 5/5 |
| | | 10 | 3 | — | 5/5 |
| 6i | (adamantyl) | 160 | 3 | 0/5 | 4/5 |
| | | 40 | 3 | 0/5 | 5/5 |
| | | 10 | 3 | — | — |

Example 2

Among the new compounds prepared, representative compounds 5e, 6c, 7a and 7c were assessed for causal prophylactic and radical cure activities in Rhesus monkeys. To protect the Rhesus monkeys, a test compound must pass a mouse toxicity test at 300 mg/kg/day for 3 consecutive days by SC administration, and mice must not lose more than 5% body weight within 30 days after receiving the test compound.

a. *Plasmodium cynomolgi* Sporozoites Induced Test in Rhesus Monkeys:

The causal prophylactic and radical curative antimalarial activity of the new derivatives 5e, 6c, 7a and 7c were assessed in a *P. cynomolgi* sporozoites challenged Rhesus monkey model. Detailed procedure of sporozoites harvest and drug tests have been described previously (J. Guan et al., *Bioorg. Med. Chem.* 23, 699-704 (2005); Q. Zhang et al., *J. Med. Chem.* 48 (20): 6472-6481 (2005)) Briefly, monkeys were randomized to control groups and experimental groups. The groupings, compounds tested, dosages, length of treatment, and routes of administration, and results are shown in Table 6. A donor monkey was inoculated intravenously with 1.3 mL freshly-thawed frozen infected red blood cells (DA310). When the donor monkey developed gametocytemia, mosquito feedings were conducted on days 13 and 14 after inoculation. The donor monkey was treated with intramuscular chloroquine hydrochloride (CQ) 10 mg/kg, once a day after the second mosquito feeding and continued for 7 days. On day 0 (beginning of assay), each of the monkeys was inoculated intravenously with 1-ml inoculum of suspension containing about 1.0×10$^6$ (one million) *P. cynomolgi* sporozoites harvested from *Anopheles dirus* mosquitoes' salivary glands previously fed on the donor monkey (See, for example, Corcoran, K D, et al. (1993) Am. J. Trop. Med. Hyg. 49:473 477, and Shanks, G D, et al. (2001) Clinical Infectious Diseases 33:1968 1974). All monkeys received treatment on days −1, 0 and 1. The control monkeys received dimethylsulfoxide (DMSO) and the experimental animals received testing compound intramusculary. After the assay, all monkeys were given standard malarial treatment. Specifically, seven-day primaquine (1.78 mg/kg) and chloroquine (10 mg/kg) were administered to treat all monkeys. The results are shown in Table 6:

TABLE 6

Causal Prophylactic Activity of 5e, 6c, 7a and 7c in *P. cynomolgi* Sporozoites Challenged Rhesus Monkeys@

| Compd # | Dose (mg/kg) | **Days Treated | Route | Results | Patency (Days Post-innocu-lation) |
|---|---|---|---|---|---|
| Control | N/A* | 1 daily for 3 days | IM | Valid Control | 8 days 8 days |
| 5e | 30 | 1 daily for 3 days | IM | Delayed +Patency for 19 to 21 days | 27 days 29 days |
| 6c | 30 | 1 daily for 3 days | IM | Delayed Patency for 54 days | 62 days |
|  |  |  |  | Delayed Patency for 86 days | 94 days |
| 7a | 30 | 1 daily for 3 days | IM | Delayed Patency for 5 to 9 days | 13 days 17 days |
| 7c | 30 | 1 daily for 3 days | IM | Delayed Patency for 13 to 32 days | 21 days 40 days |

@Two monkeys per dose group.
*At the same volume as other experimental groups. Maximum DMSO volume per site is 1 mL of 2 injection sites (one in each thigh).
**Drugs were dissolved in DMSO and given on days before, on the day and a day after (−1, 0, +1 day) sporozoites inoculation.
+First day the parasite can be detected in blood smears after infection.

The results indicated that all compounds tested displayed protection in monkeys. Carboxamide derivative 7a showed weak causal prophylactic activity in Rhesus test, prolonged the patency for 5 days to one monkey and 9 days for the other. Carboxamide 7c, however, showed superior protective activity than that of 7a, delayed patency 13 days for one of the treated monkeys and 32 days for the other. Benzyloxy derivative 5e was about equal in causal prophylactic activity to 7c, delayed patency for treated monkey from 19 to 21 days at doses of 30 mg/kg/day for 3 days by IM. Among the 4 compounds tested, 6c exhibited the most potent causal prophylactic activity, delayed patency for 54 days in one treated monkey and the other for 86 days.

The monkeys were only treated for 3 days in the experiments, instead of 7 days for 8-aminoquinoline antimalarials, such as primaquine and tafenoquine, in the reported protocols (E. Beutler, *Blood,* 14 (2), 103-139 (1959); P. Phillips-Howard et al., *Drug Safety* 12:370-383 (1995); P. Schlagenhauf, *J Travel Med* 6:122-123 (1999)). Thus, longer treatment with the test compounds can lead to higher rate of cures. In addition, no adverse side effects was observed in the monkeys treated with the test compounds at the level of 30 mg/kg×3 days, indicating that longer treatments would be tolerated.

b. Radical Cure Test in Rhesus Monkeys:

Assessment of radical curative activity of the test compounds was carried out using the monkeys that developed parasitemia during the causal prophylactic experiments when the test compounds showed no or weak activity. Monkeys were treated with chloroquine (10 mg/kg/day) by oral for 7 consecutive days and the test compounds by IM for 3 consecutive days after the parasitemia level reached 5,000 parasites/mm³. Chloroquine (CQ) at 10 mg/kg/day×7 days eliminates the blood stage parasites, but not the liver stage hypnozoites. Compounds with antihypnozoite activity will delay the relapse or radically cure the infection. To evaluate the radical curative properties, daily blood samples were followed for 21 days, 3 times per week for 4 weeks, and then 2 times weekly until 100 days after the last day of test compound administration. Parasite clearance should occur in all animals treated with chloroquine. Relapse is expected in the control group. Relapse in the treated group indicates failure of the test compounds. Monkeys showed no relapse after 100 days are considered radically cured. Relapses of the control monkeys were treated with chloroquine once daily for 7-days and observed for a second relapse. Relapse in experimental animals and the second relapse of the control monkeys were treated with the standard 7-day oral CQ (chloroquine) and primaquine (1.78 mg base/kg). After standard treatment, blood smears were monitored daily for 4 consecutive days of negative results and 2 times weekly for 2 weeks. The results are shown in Table 7.

TABLE 7

Radical Curative Activity of Compounds in 5e, 5c, 7a and 7c Relapsed Rhesus Monkeys.

| Group No. | Drug 1 | Drug 2 | Dose (mg/kg) | # Doses per Day | Route | Results | Days Post-treatment |
|---|---|---|---|---|---|---|---|
| 1 | CQ, 10 mg/kgx7, po | None |  |  | Oral | Relapse | 9 days 9 days |
| 2 | CQ, 10 mg/kgx7, po | 5e | 30 | 1 daily for 3 days | IM | Delayed relapse | 35 days 33 days |
| 3 |  | 6c | 30 | 1 daily for 3 days | IM | Delayed relapse | 66 days 91 days |
| 4 |  | 7a | 30 | 1 daily for 3 days | IM | Delayed relapse Radical Cure | 16 days Radical cure |
| 5 |  | 7c | 40 | 1 daily for 3 days | IM | Delayed relapse | 29 days 32 days |

All of the compounds tested delayed relapse compared to the control group. One out of two monkeys treated with 7a was cured. The other treated monkey showed delayed relapse for 16 days, 7 days longer as compared with untreated control animals. Compound 7c delayed relapse in one monkey for 29 and the other for 32 days, 20 and 23 days longer, respectively, as compared with control animals. Compound 6c was more active than 5e, 7a and 7c in radical curative efficacy test.

Having thus described exemplary embodiments of the present invention, it should be noted by those skilled in the art that the written disclosures are exemplary only and that various other alternatives, adaptations, and modifications can be made within the scope of the present invention.

What is claimed is:

1. A compound having the formula I:

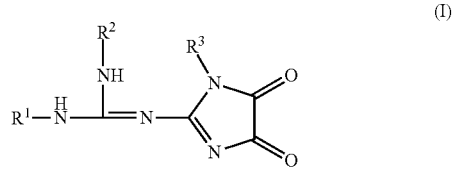

or a tautomer thereof, or their pharmaceutically acceptable salts, wherein:
R[1] is aryl or heteroaryl, each optionally substituted with one or more R[1a];
each R[1a] is independently selected from the group consisting of hydroxyl, carboxyl, halo, aralkyl, amino, alkylamino, dialkylamino, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy, optionally substituted with up to 5 fluoro;
R[2] is an optionally substituted substituent selected from the group consisting of $C_{1-10}$ alkyl, $C_{2-10}$ alkenyl, $C_{3-10}$ cycloalkyl$(CH_2)_n$—, aryl$(CH_2)_n$—, heteroaryl$(CH_2)_n$—, alkylaryl, heterocyclyl$(CH_2)_n$—, aminoalkyl, $R^{2a}R^{2b}N(CH_2)_n$—, or R[2] is $R^5O$—;
n is an integer selected from 0, 1, 2, 3, 4, 5, 6, or 7;
R[2a] is selected from the group consisting of hydrogen, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy optionally substituted with up to 5 fluoro;
R[2b] is selected from the group consisting of hydrogen, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy optionally substituted with up to 5 fluoro;
R[3] is $C_{1-10}$ alkyl optionally substituted with up to 5 fluoro; and
R[5] is an optionally substituted substituent selected from the group consisting of $C_{1-10}$ alkyl, $C_{2-10}$ alkenyl, $C_{3-10}$ cycloalkyl$(CH_2)_n$—, aryl$(CH_2)_n$—, heteroaryl$(CH_2)_n$—, alkylaryl, heterocyclyl$(CH_2)_n$—, aminoalkyl, and $R^{2a}R^{2b}N(CH_2)_n$—.

2. The compound of claim 1,
wherein:
R[1] is phenyl optionally substituted with one or more R[1a];
each R[1a] is independently selected from the group consisting of halo, $C_{1-3}$ alkyl optionally substituted with up to 5 fluoro, and $C_{1-3}$ alkoxy, optionally substituted with up to 5 fluoro;
R[2] is selected from the group consisting of $C_{1-6}$ alkyl, $C_{2-6}$ alkenyl, $C_{3-7}$ cycloalkyl, aryl, heteroaryl, heterocyclyl$(CH_2)_n$—, aminoalkyl, $R^{2a}R^{2b}N(CH_2)_n$—, $C_{1-6}$ alkylO—, $C_{2-6}$ alkenylO—, $C_{3-10}$ cycloalkylO—, arylO—, heteroarylO—, heterocyclylO—, and $R^{2a}R^{2b}N(CH_2)_nO$—,
n is an integer selected from 1, 2, 3, 4, 5, or 6;
R[2a] is selected from the group consisting of hydrogen, and $C_{1-6}$ alkyl optionally substituted with up to 5 fluoro, and $C_{1-6}$ alkoxy optionally substituted with up to 5 fluoro;
R[2b] is selected from the group consisting of alkoxycarbonyl, and $C_{1-6}$ alkyl optionally substituted with up to 5 fluoro; and
R[3] is $C_{1-4}$ alkyl.

3. The compound of claim 1, wherein R[2] is isopropyl.

4. The compound of claim 1,
wherein:
R[1] is phenyl optionally substituted with one or more R[1a];
each R[1a] is independently selected from the group consisting of halo, $C_{1-3}$ alkyl optionally substituted with up to 5 fluoro, and $C_{1-3}$ alkoxy, optionally substituted with up to 5 fluoro;
R[2] is $R^5O$—,
R[5] is selected from the group consisting of $C_{3-7}$ cycloalkyl, and $C_{1-6}$ alkyl, each optionally substituted with up to 3 fluoro; and
R[3] is $C_{1-4}$ alkyl.

5. The compound of claim 1 having the formula Ia, or Ic:

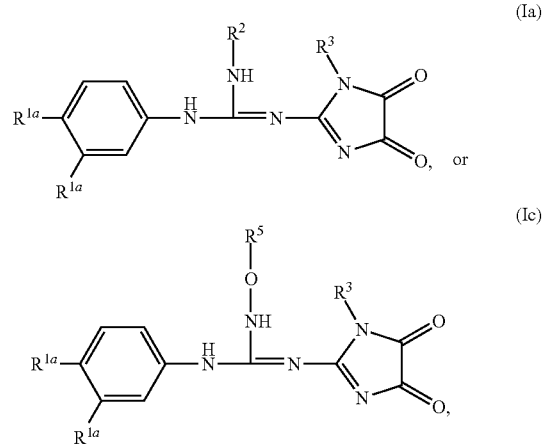

or a tautomer thereof, or their pharmaceutically acceptable salts.

6. The compound of claim 5 having the formula Iaa, or Icc:

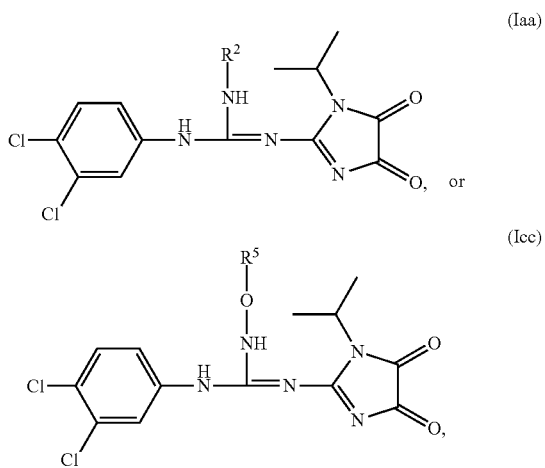

or a tautomer thereof, or their pharmaceutically acceptable salts,
wherein:
R[2] is selected from the group consisting of $C_{1-6}$ alkyl, $C_{3-10}$ cycloalkyl, aryl, heteroaryl, heterocyclyl, $C_{3-10}$ cycloalkyl$CH_2$—, aryl$CH_2$—, heteroaryl$CH_2$—, heterocyclyl$CH_2$—, $R^{2a}R^{2b}N(CH_2)_n$—;
n is an integer selected from 1, 2, 3, 4, 5, or 6;
R[2a] is selected from the group consisting of hydrogen, and $C_{1-6}$ alkyl optionally substituted with up to 5 fluoro, and $C_{1-6}$ alkoxy optionally substituted with up to 5 fluoro;
R[2b] is selected from the group consisting of alkoxycarbonyl, and $C_{1-6}$ alkyl optionally substituted with up to 5 fluoro; and
R[5] is selected from the group consisting of $C_{1-6}$ alkyl, $C_{1-6}$ alkyl, $C_{3-10}$ cycloalkyl, aryl, heteroaryl, heterocyclyl, $C_{3-10}$ cycloalkyl$CH_2$—, aryl$CH_2$—, each optionally substituted with up to 3 fluoro.

7. The compound of claim 6, wherein R[2] is methyl, ethyl, isopropyl, tert-butyl, allyl, benzyl, neopentyl, or phenyl.

8. A method for making a compound of formula II:

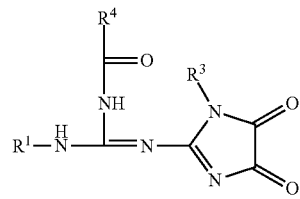
(II)

or a tautomer thereof, or their pharmaceutically acceptable salts,
comprising intermixing a compound of formula IIa:

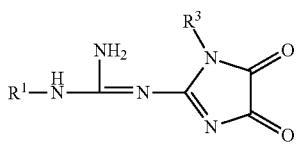
(IIa)

with a compound of formula A:

(A)

in the presence of a base,
wherein:
the base is selected from the group consisting of triethyl amine, diisopropyul ethyl amine, dimethyl amino pyridine (DMAP), DBU, DBN, sodium carbonate, potassium carbonate, lithium carbonate, calcium carbonate, magnesium carbonate, sodium bicarbonate, potassium bicarbonate, lithium bicarbonate, and combinations thereof;
X is halo or $R^4C(=O)O-$;
$R^1$ is aryl or heteroaryl, each optionally substituted with one or more $R^{1a}$;
each $R^{1a}$ is independently selected from the group consisting of hydroxyl, carboxyl, halo, aralkyl, amino, alkylamino, dialkylamino, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy, optionally substituted with up to 5 fluoro;
$R^3$ is $C_{1-10}$ alkyl optionally substituted with up to 5 fluoro; and
$R^4$ is selected from the group consisting of aryl, heteroaryl, $C_{3-7}$ cycloalkyl, and $C_{1-6}$ alkyl, each optionally substituted with up to 5 fluoro.

9. The method of claim 8, wherein $R^3$ is isopropyl.

10. A method for making a compound of formula III:

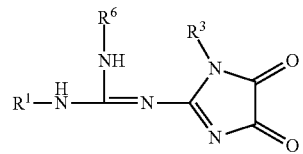
(III)

or a tautomer thereof, or their pharmaceutically acceptable salts,
comprising intermixing a compound of formula IIIa:

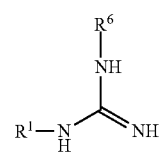
(IIIa)

with a compound of formula B:

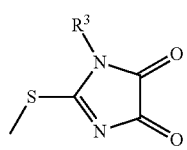
(B)

under heating conditions,
wherein:
$R^1$ is aryl or heteroaryl, each optionally substituted with one or more $R^{1a}$;
each $R^{1a}$ is independently selected from the group consisting of hydroxyl, carboxyl, halo, aralkyl, amino, alkylamino, dialkylamino, alkoxycarbonyl, alkylsulfonyl, heterocycle, aryl, $C_{3-7}$ cycloalkyl, $C_{1-6}$ alkyl optionally substituted with up to 5 fluoro, and $C_{1-6}$ alkoxy, optionally substituted with up to 5 fluoro;
$R^3$ is $C_{1-10}$ alkyl optionally substituted with up to 5 fluoro;
$R^6$ is selected from the group consisting of $C_{1-6}$ alkyl, $C_{3-10}$ cycloalkyl, aryl, heteroaryl, heterocyclyl, $C_{3-10}$ cycloalkylCH$_2$—, arylCH$_2$—, heteroarylCH$_2$—, heterocyclylCH$_2$—, $R^{6a}R^{6b}N(CH_2)_n$—;
n is an integer selected from 1, 2, 3, 4, 5, or 6;
$R^{6a}$ is selected from the group consisting of hydrogen, and $C_{1-6}$ alkyl optionally substituted with up to 5 fluoro, and $C_{1-6}$ alkoxy optionally substituted with up to 5 fluoro; and
$R^{6b}$ is selected from the group consisting of alkoxycarbonyl, and $C_{1-6}$ alkyl optionally substituted with up to 5 fluoro.

11. The method of claim 10,
wherein:
$R^1$ is phenyl optionally substituted with one or more $R^{1a}$;
each $R^{1a}$ is independently selected from the group consisting of halo, $C_{1-3}$ alkyl optionally substituted with up to 5 fluoro, and $C_{1-3}$ alkoxy, optionally substituted with up to 5 fluoro;
$R^6$ is selected from the group consisting of $C_{1-6}$ alkyl, $C_{2-6}$ alkenyl, $C_{3-7}$ cycloalkyl, aryl, heteroaryl, heterocyclyl (CH$_2$)$_n$—, aminoalkyl, $C_{1-10}$ alkylC(=O)—, $R^{6a}R^{6b}N$ (CH$_2$)$_n$—, $C_{1-6}$ alkylO—, $C_{2-6}$ alkenylO—, $C_{3-10}$ cycloalkylO—, arylO—, heteroarylO—, heterocyclylO—, $C_{1-6}$ alkylC(=O)O—, -and $R^{6a}R^{6b}N(CH_2)_nO$—, n is an integer selected from 1, 2, 3, 4, 5, or 6;

$R^{6a}$ is selected from the group consisting of hydrogen, and $C_{1-6}$ alkyl optionally substituted with up to 5 fluoro, and $C_{1-6}$ alkoxy optionally substituted with up to 5 fluoro;

$R^{6b}$ is selected from the group consisting of alkoxycarbonyl, and $C_{1-6}$ alkyl optionally substituted with up to 5 fluoro; and $R^3$ is $C_{1-4}$ alkyl.

12. The method of claim 11, wherein $R^3$ is isopropyl.

13. A method of treating, preventing, or inhibiting malaria or a disease or disorder associated with malaria or a *Plasmodium* parasite, comprising administering a therapeutically effective amount of the compound of claim 1 to a subject in need thereof.

14. The method of claim 13, wherein the compound is administered intramuscularly, orally, or transdermally.

15. The method of claim 13 further comprising administering to the subject a supplementary active compound, wherein the supplementary active compound is an antimalarial, an antibacterial, or an anti-inflammatory agent.

16. A composition comprising the compound of claim 1 and a pharmaceutically acceptable carrier.

17. A compound represented by structural formula 5, or 6,

5

6 or a pharmaceutically acceptable equivalent or pharmaceutically acceptable salt of said compound;

wherein R is an optionally substituent selected from the group consisting of alkyl, aryl, cycloalkyl, heterocycloalkyl, heteroaryl, alkylaryl, heterocyclic rings, and aminoalkyl.

18. The compound of claim 17, wherein R is an optionally substituted substituent selected from the group consisting of alkyl, aryl, aminoalkyl, and hetrocyclic ring;

wherein the alkyl substituent or any alkyl portion of the substituents is saturated or unsaturated and/or aliphatic or branched;

or a pharmaceutically acceptable equivalent or pharmaceutically acceptable salt of said compound.

19. The compound of claim 17, wherein R is methyl, ethyl, isopropyl, t-butyl, allyl, benzyl, neopentyl, or phenyl.

20. The compound of claim 17, wherein said compound is represented by structure 6, and wherein R is isopropyl;

or a pharmaceutically acceptable equivalent or pharmaceutically acceptable salt of said compound.

* * * * *